United States Patent
Scopton et al.

(10) Patent No.: US 9,421,063 B2
(45) Date of Patent: Aug. 23, 2016

(54) ENDOSCOPIC DEVICES AND RELATED METHODS OF USE

(71) Applicants: Paul M. Scopton, Winchester, MA (US); John A. Griego, Blackstone, MA (US); Stephen J. Perry, Shirley, MA (US); William J. Shaw, Cambridge, MA (US)

(72) Inventors: Paul M. Scopton, Winchester, MA (US); John A. Griego, Blackstone, MA (US); Stephen J. Perry, Shirley, MA (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 425 days.

(21) Appl. No.: 13/888,150

(22) Filed: May 6, 2013

(65) Prior Publication Data

US 2013/0317500 A1    Nov. 28, 2013

Related U.S. Application Data

(63) Continuation of application No. 12/612,973, filed on Nov. 5, 2009, now Pat. No. 8,454,597, which is a continuation of application No. 11/055,604, filed on Feb. 11, 2005, now Pat. No. 7,632,266.

(60) Provisional application No. 60/612,781, filed on Sep. 27, 2004, provisional application No. 60/544,348, filed on Feb. 17, 2004.

(51) Int. Cl.
*A61B 18/14* (2006.01)
*A61B 17/32* (2006.01)
(Continued)

(52) U.S. Cl.
CPC ....... *A61B 18/1482* (2013.01); *A61B 17/3207* (2013.01); *A61B 17/320016* (2013.01); *A61B 17/32056* (2013.01); *A61B 17/3478* (2013.01); *A61B 18/1492* (2013.01); *A61M 25/0069* (2013.01); *A61B 17/320783* (2013.01); *A61B 2017/22072* (2013.01); *A61B 2017/22082* (2013.01); *A61B 2018/00482* (2013.01); *A61B 2217/005* (2013.01); *A61B 2218/002* (2013.01);
(Continued)

(58) Field of Classification Search
CPC .............. A61B 18/14; A61B 18/1477; A61B 2018/0016; A61B 2018/00345; A61B 2018/00571; A61B 2018/00577; A61B 2018/00589; A61B 2018/00595; A61B 2018/00601; A61B 2018/00607; A61B 2018/1417; A61B 2018/1435
See application file for complete search history.

(56) References Cited

U.S. PATENT DOCUMENTS

| | | | | |
|---|---|---|---|---|
| 4,532,924 A | * | 8/1985 | Auth | ....................... A61B 18/14 606/50 |
| 5,085,659 A | * | 2/1992 | Rydell | ................... A61B 10/04 606/170 |

(Continued)

FOREIGN PATENT DOCUMENTS

DE           3743139 A1     7/1989

*Primary Examiner* — Michael Peffley
(74) *Attorney, Agent, or Firm* — Bookoff McAndrews, PLLC

(57) ABSTRACT

Embodiments of the invention include a medical device including a handle portion, an end effector assembly, an elongate member connecting the handle portion and the end effector assembly, and one or more treatment devices extendable through the elongate member and end effector assembly. The end effector assembly includes an electrode assembly configured to cauterize tissue. The treatment devices may include an elongate cutting member with a safety tip. The treatment devices may include a multi-lumen catheter with a lumen configured to deliver fluid and another lumen configured to accommodate an injection needle, a cutting member, or other therapeutic or diagnostic devices.

7 Claims, 30 Drawing Sheets

(51) Int. Cl.
*A61B 17/3205* (2006.01)
*A61B 17/3207* (2006.01)
*A61B 17/34* (2006.01)
*A61M 25/00* (2006.01)
*A61B 17/22* (2006.01)
*A61B 18/00* (2006.01)

(52) U.S. Cl.
CPC ..... *A61B 2218/007* (2013.01); *A61M 25/0084* (2013.01); *A61M 2025/004* (2013.01); *A61M 2025/0036* (2013.01)

(56) References Cited

U.S. PATENT DOCUMENTS

| | | | |
|---|---|---|---|
| 5,334,193 A | 8/1994 | Nardella | |
| 5,336,222 A * | 8/1994 | Durgin, Jr. | A61B 18/1477 604/21 |
| 5,342,357 A * | 8/1994 | Nardella | A61B 18/1206 606/38 |
| 5,403,311 A * | 4/1995 | Abele | A61B 18/1477 604/21 |
| 5,836,947 A | 11/1998 | Fleischman et al. | |
| 5,846,241 A | 12/1998 | Kittur et al. | |
| 6,063,080 A | 5/2000 | Nelson et al. | |
| 6,106,524 A | 8/2000 | Eggers et al. | |
| 6,149,620 A * | 11/2000 | Baker | A61B 18/12 604/22 |
| 6,179,832 B1 * | 1/2001 | Jones | A61B 18/1492 606/32 |
| 6,217,576 B1 | 4/2001 | Tu et al. | |
| 6,221,039 B1 | 4/2001 | Durgin et al. | |
| 6,325,797 B1 | 12/2001 | Stewart et al. | |
| 6,610,056 B2 | 8/2003 | Durgin et al. | |
| 6,712,812 B2 | 3/2004 | Roschak et al. | |
| 6,733,496 B2 | 5/2004 | Sharkey et al. | |
| 6,770,066 B1 | 8/2004 | Weaver et al. | |
| 7,537,594 B2 | 5/2009 | Sartor | |
| 2002/0095151 A1 * | 7/2002 | Dahla | A61B 18/148 606/41 |
| 2003/0032918 A1 | 2/2003 | Quinn | |

* cited by examiner

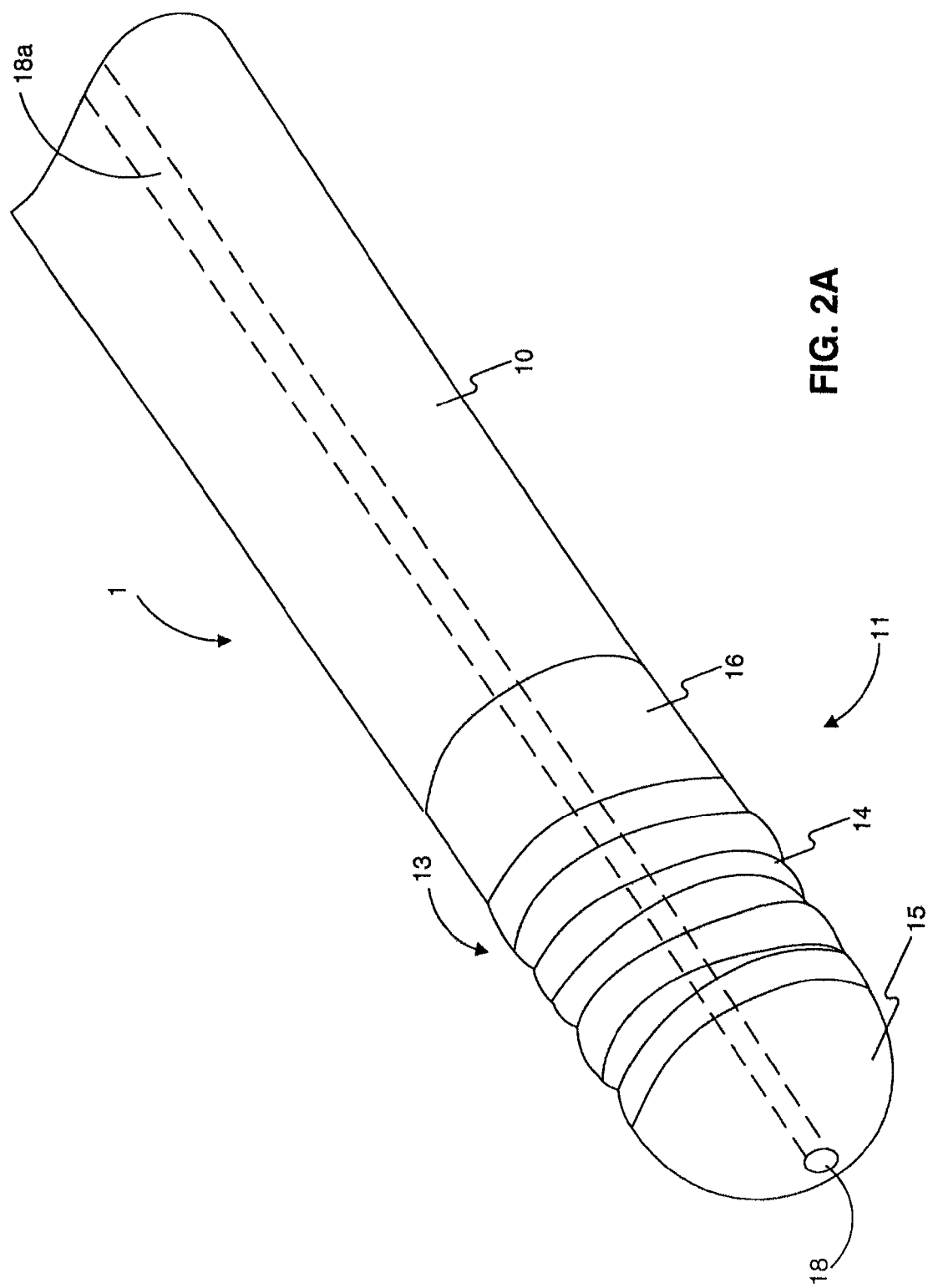

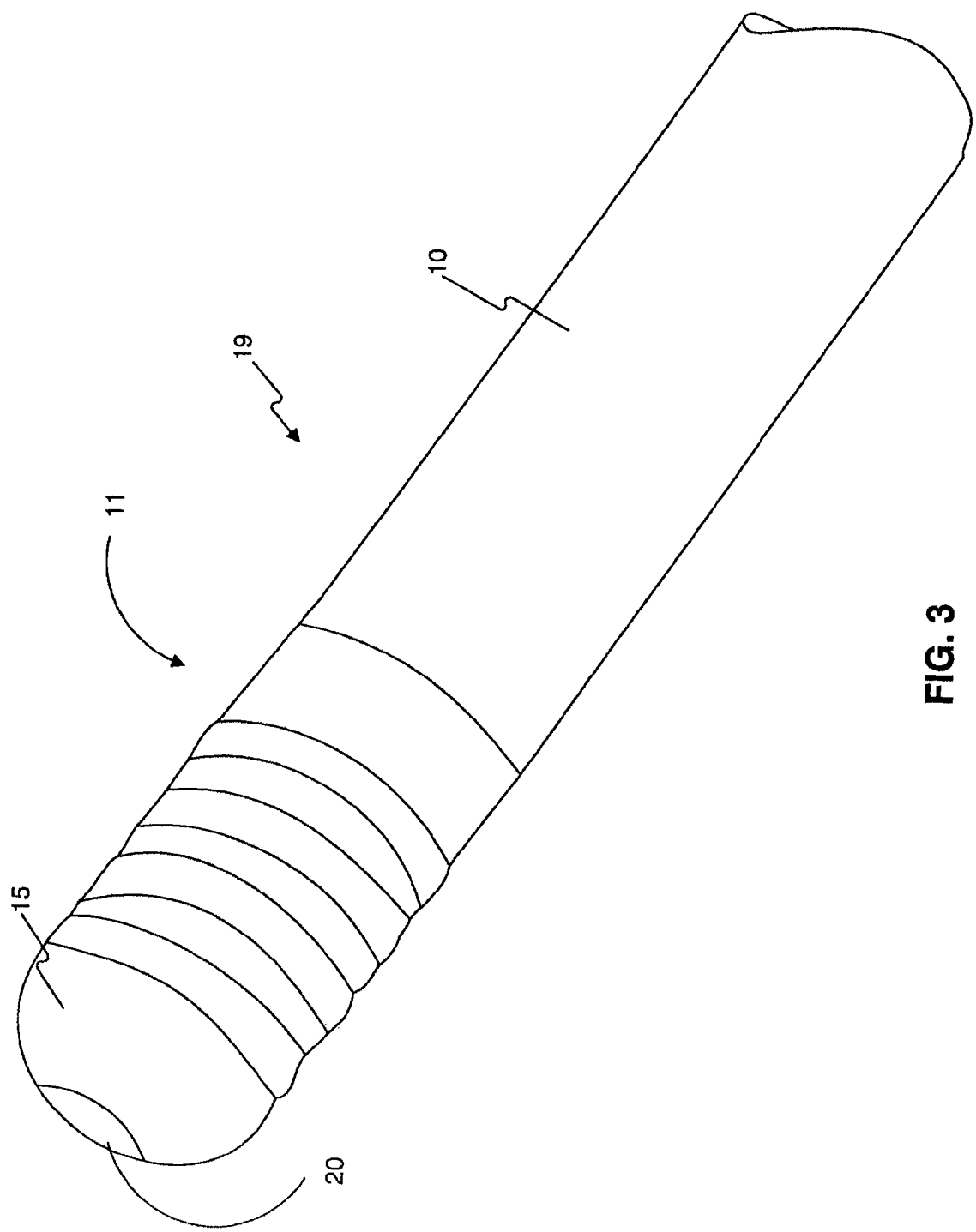

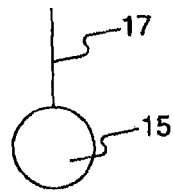
FIG. 7A
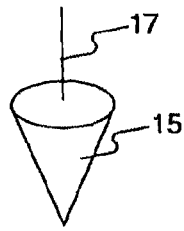
FIG. 7B
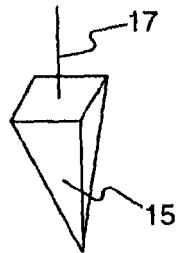
FIG. 7C
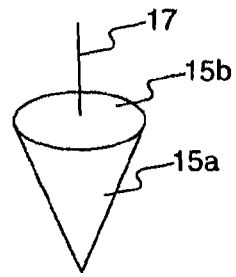
FIG. 7D
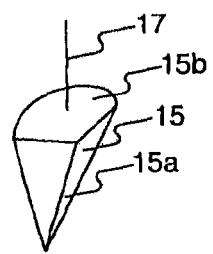
FIG. 7E
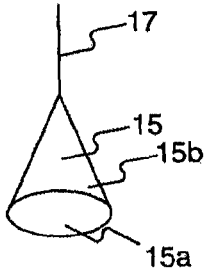
FIG. 7F
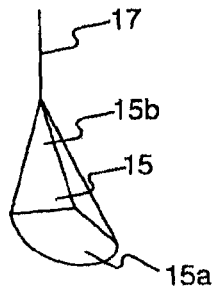
FIG. 7G
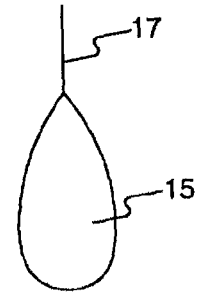
FIG. 7H
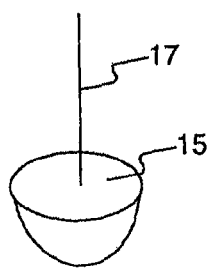
FIG. 7I
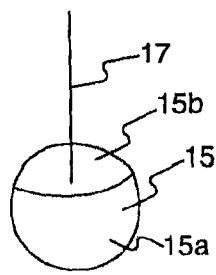
FIG. 7J
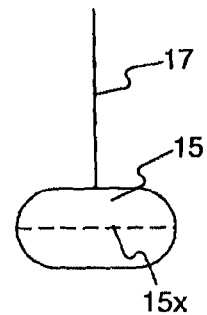
FIG. 7K
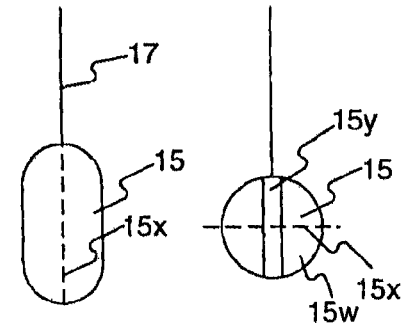
FIG. 7L   FIG. 7M

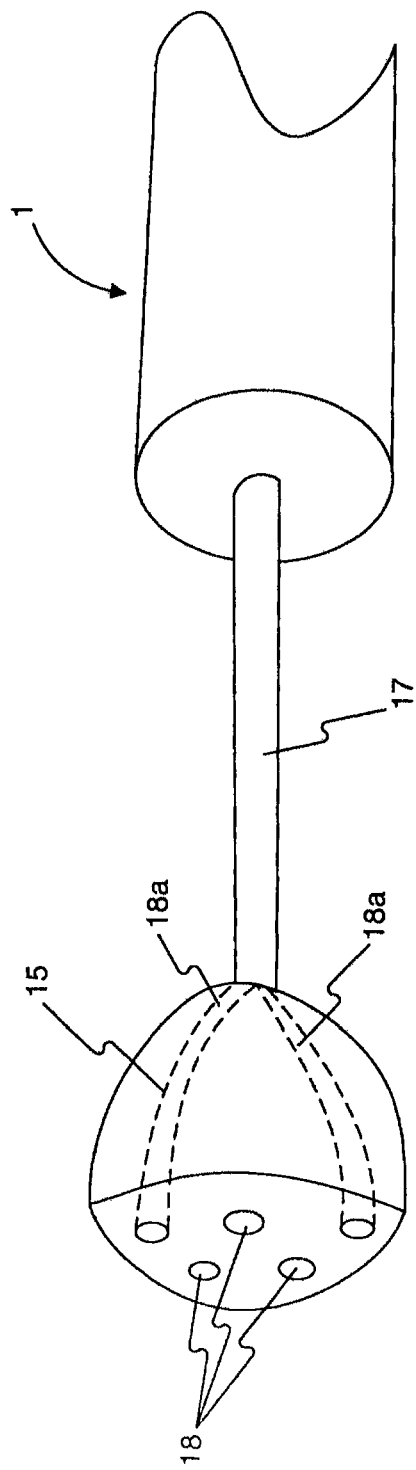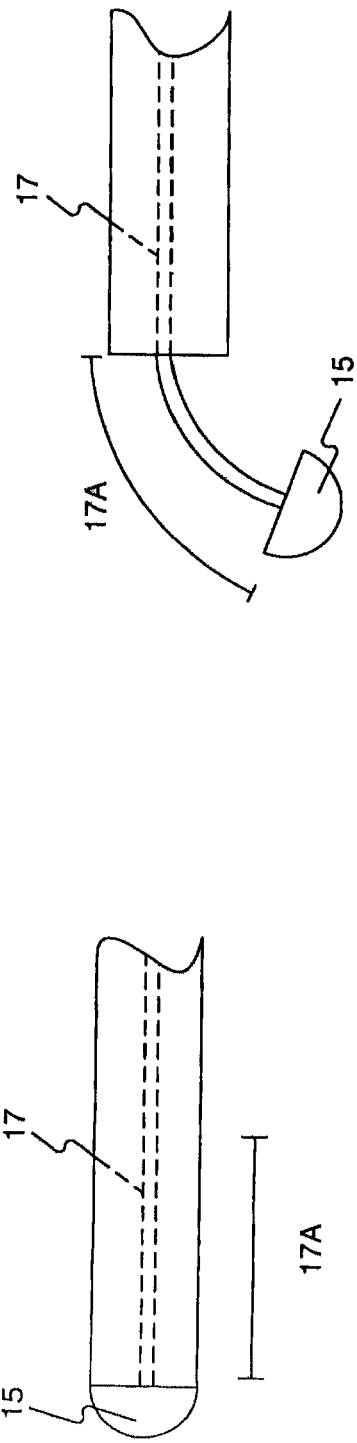
FIG. 8
FIG. 9A
FIG. 9B

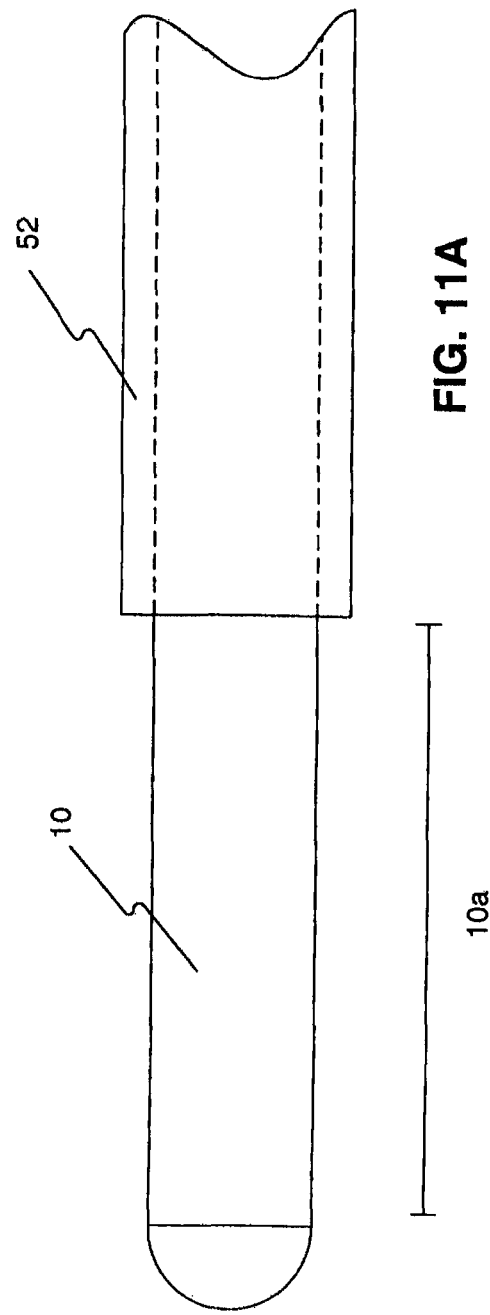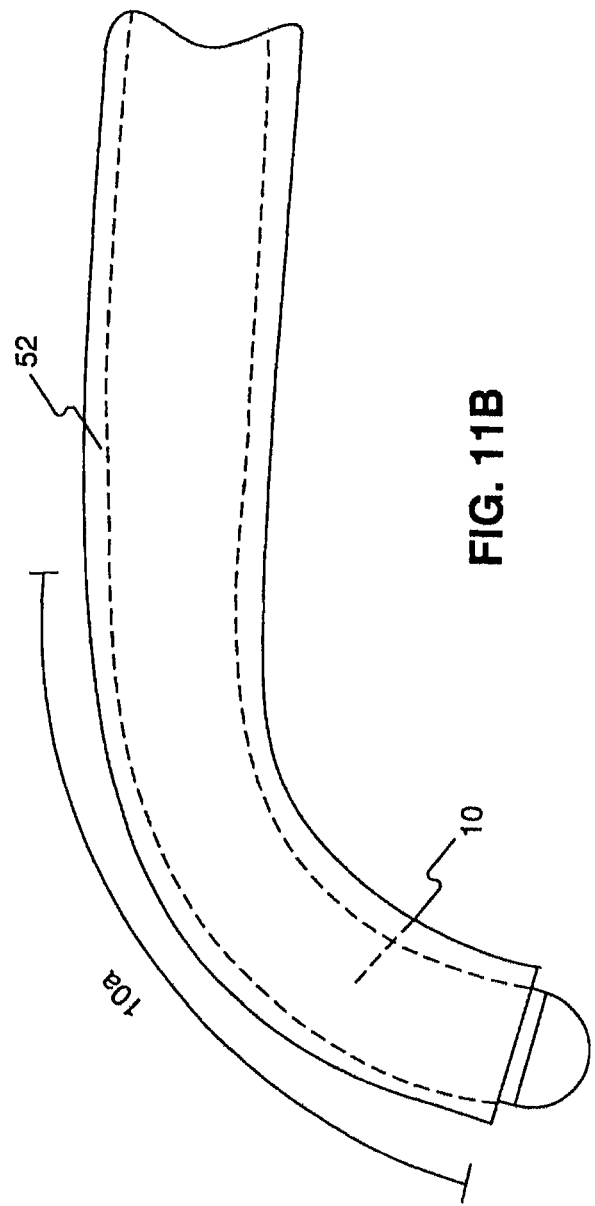
FIG. 11A
FIG. 11B

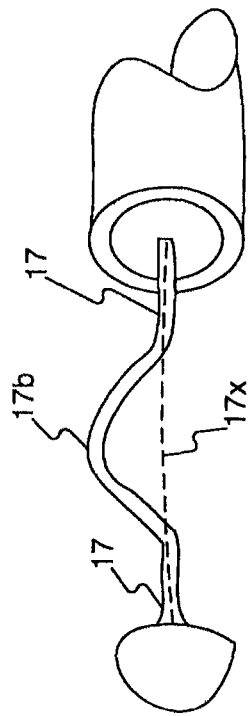
FIG. 15B
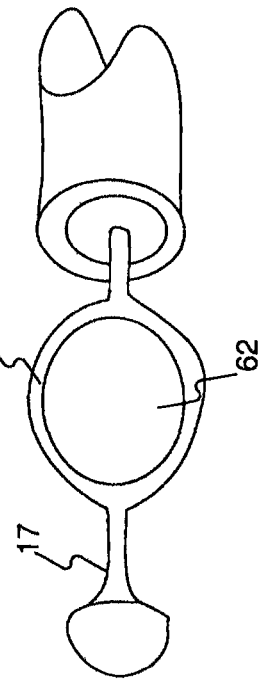
FIG. 15D
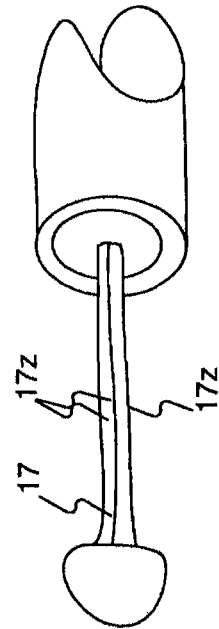
FIG. 15F
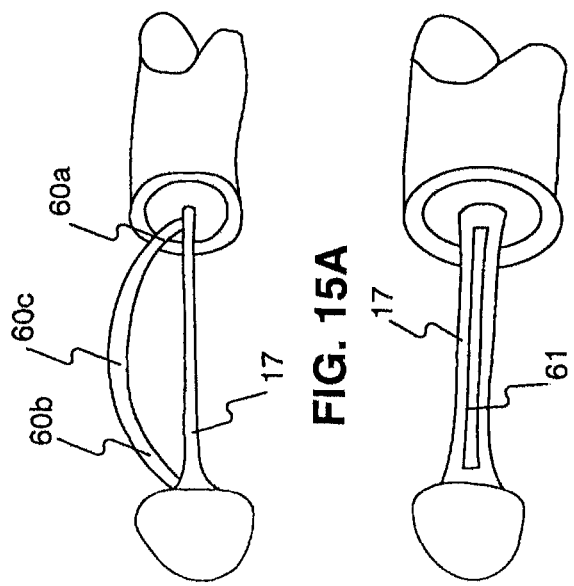
FIG. 15A
FIG. 15C
FIG. 15E
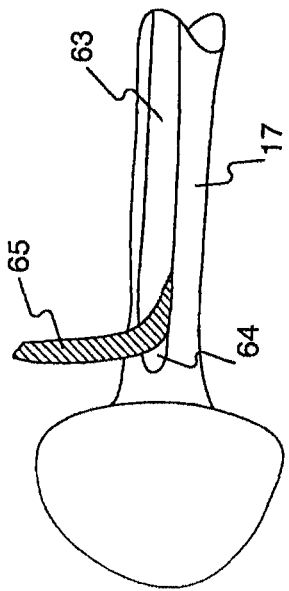

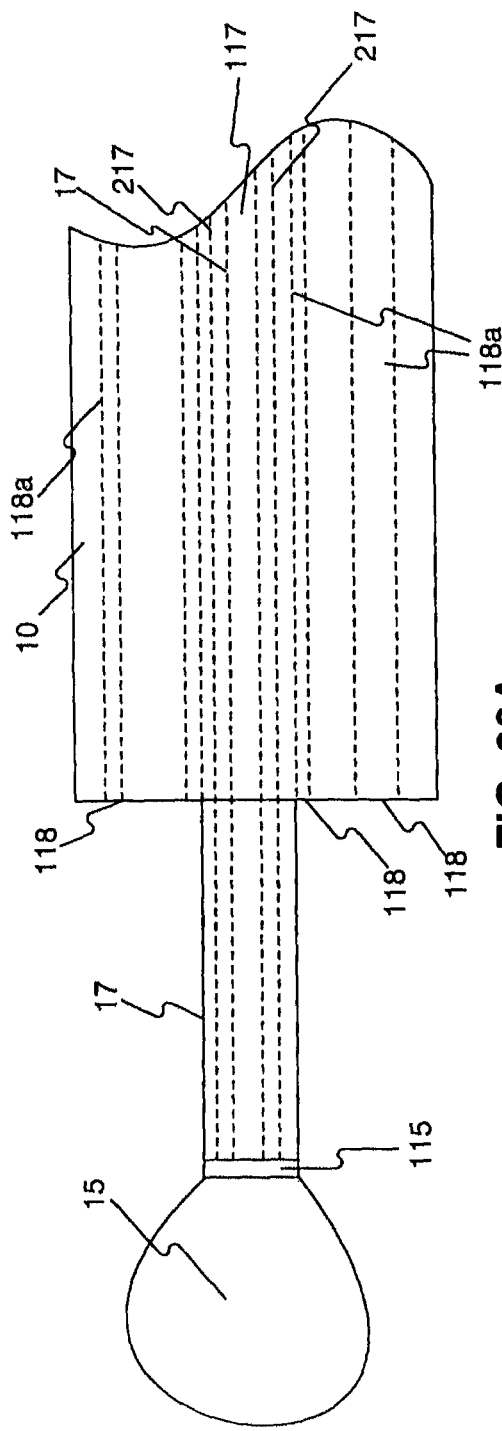
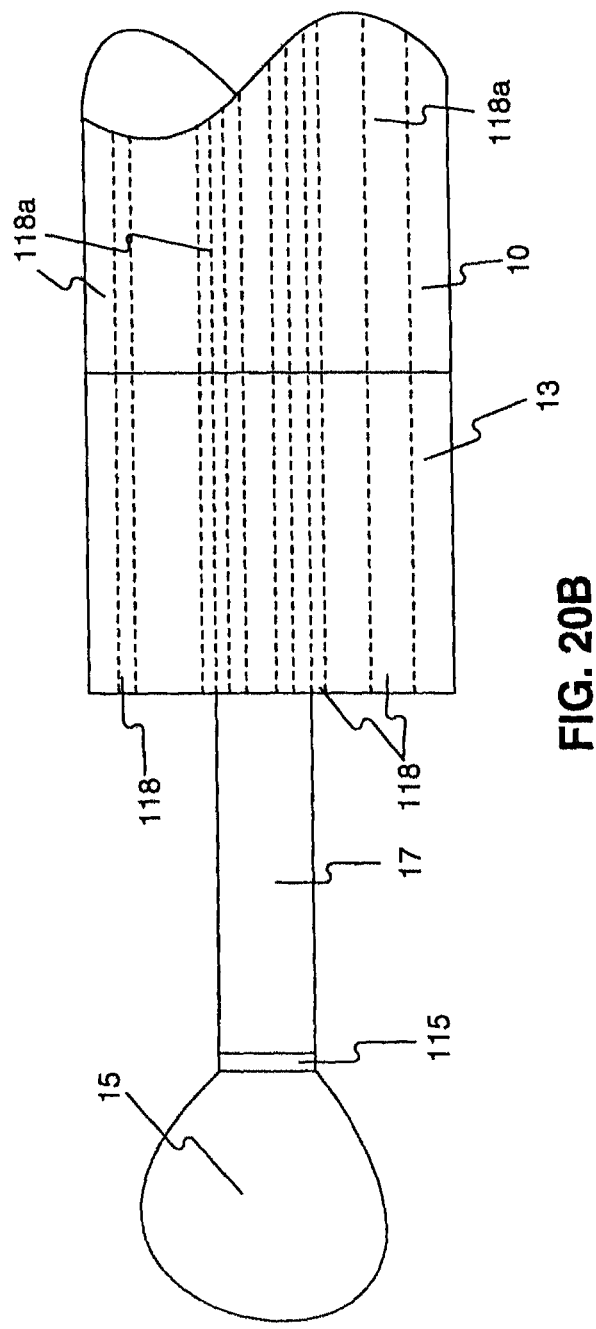
FIG. 20A
FIG. 20B

ENDOSCOPIC DEVICES AND RELATED METHODS OF USE

CROSS-REFERENCE TO RELATED APPLICATIONS

This application is a continuation of U.S. application Ser. No. 12/612,973, filed Nov. 5, 2009, now U.S. Pat. No. 8,454,597, which is a continuation of U.S. application Ser. No. 11/055,604, filed Feb. 11, 2005, now U.S. Pat. No. 7,632,266, which claims the benefits of priority under 35 U.S.C. §§119(e), 120 to U.S. Provisional Patent Application No. 60/544,348, filed Feb. 17, 2004, to Paul SCOPTON and John A. GRIEGO entitled ENDOSCOPIC DEVICE AND RELATED METHODS OF USE, and to U.S. Provisional Patent Application No. 60/612,781, filed Sep. 27, 2004, to Paul SCOPTON, John A. GRIEGO, Stephen J. PERRY, and William SHAW entitled ENDOSCOPIC DEVICES AND RELATED METHODS OF USE, the entirety of all of which are incorporated herein by reference.

DESCRIPTION OF THE INVENTION

1. Field of the Invention

Embodiments of the invention include a medical device including a handle portion, an end effector assembly, an elongate member connecting the handle portion and the end effector assembly, and one or more treatment devices extendable through the elongate member and end effector assembly. The end effector assembly includes an electrode assembly configured to cauterize tissue. The treatment devices may include an elongate cutting member with a safety tip. The treatment devices may include a multi-lumen catheter with a lumen configured to deliver fluid and another lumen configured to accommodate an injection needle, a cutting member, or other therapeutic or diagnostic devices.

2. Background of the Invention

Endoscopic methods are commonly used for diagnosis and/or treatment of the gastrointestinal tract. For example, there are several methods of treating esophageal cancer known as endoscopic mucosal resection. Endoscopic mucosal resection may include snaring and then excising sessile adenomas (i.e., tumors attached to a bodily surface) in the esophageal tract. If the adenoma is flat against the esophageal tract, thus making it difficult to snare and excise, one of several methods may be used to raise the flat adenoma so that it may be snared and excised. One method includes using forceps to raise the flat adenoma. Another method includes using a vacuum to raise the flat adenoma. A further method includes injecting saline into the submucosa so as to raise the flat adenoma. If, during saline injection, it is determined that the adenoma is attached to multiple esophageal tissue layers, additional methods may be required to remove the adenoma. Once the adenoma is excised, bleeding into the esophageal tract may result from the portion of the esophageal tissue from which the adenoma was removed.

These, and other medical procedures (e.g., staining, marking, and identifying tissue), may involve making an incision in body tissue and controlling any consequent bleeding. When performing these procedures, it may be desirable to minimize both tissue trauma during incision and the time required to stop internal bleeding. Minimally invasive or least invasive surgical techniques, such as laparoscopic, endoscopic, or arthoroscopic techniques, are sometimes used because body tissue is usually traumatized less by those techniques than by more invasive conventional techniques. Electrosurgical methodologies, sometimes used in conjunction with the minimally or least invasive techniques, allow the making of an incision and the stopping or stemming of bleeding with less attendant tissue trauma and greater control than do conventional modalities.

Several medical instruments may be used to make an incision and stem consequent bleeding. In accordance with one modality that is suited for application in the gastrointestinal tract, a physician initially positions a flexible endoscope in the patient with its distal end proximate to an incision site, and inserts a device for making an incision through a working port of the endoscope to the incision site. The physician can also insert an irrigator through a working port in the endoscope to clear the area by administering water or saline solution as a precursor to any attempts to make an incision or stop bleeding. The irrigator can also be used to inject water or saline solution between tissue layers so as to separate the tissue layers.

If the instrument being used for irrigation is like the Injection Gold Probe™ hemostasis catheter manufactured by Boston Scientific Corporation, the physician can then cauterize a bleeding vessel using a distally positioned hemostat. Such instruments are constructed to be employed through a working port of an endoscope to seal potential bleeding sites in the gastrointestinal tract. Alternatively, the physician can retract the irrigating catheter and insert an elongated needle through the endoscope to inject a vasoconstrictor into the vessel to slow hemorrhaging. Then the physician can remove the elongated needle and reinsert the hemostat to finish the operation.

Some hemostats use mono-electropolar electrodes in which one electrode may be carried by a catheter to a site while the other electrode may be an exterior ground plate placed in or on a patient. The above-mentioned Gold Probe™ hemostat is an example of a device that supplies a suitable current density and wave form of radio frequency energy to perform electro-coagulation or electro-cauterization. It utilizes a catheter with a bipolar electrode assembly located on a flexible shaft formed of a ceramic cylinder having a hemispherical end. The ceramic tip includes a pair of spaced gold spiral electrodes applied to its cylindrical surface and domed end. RF energy applied to the electrodes produces a current through adjacent tissue that heats and cauterizes the hemorrhaging vessel which is contacted by the tip of the catheter. The Injection Gold Probe™ hemostasis catheter also permits needle injection with a single catheter.

The aforementioned methods, while effective, have certain drawbacks. As physicians sometimes use different catheters to perform different functions, for example, use one catheter to make an incision and another to perform hemostasis or irrigation, the exchange of catheters to provide different functions extends the time to complete therapy, increases the risk to the patient and also increases patient discomfort. Consequently, physicians have to weigh the time, complexity and benefits of interchanging single or dual purpose catheters to change treatment modalities against whatever disadvantage may result by working with a single catheter.

U.S. Pat. Nos. 5,336,222, 5,403,311, and 6,325,800 B1, and U.S. Patent Application No. 2002/0111623 A1, the contents of all of which are incorporated herein, each disclose an integrated catheter assembly for enabling diverse in situ therapies which includes a catheter with an irrigation fluid lumen, a distal tip portion that acts as a hemostat, and a needle for injection therapy.

SUMMARY OF THE INVENTION

In accordance with the invention, an embodiment of the invention includes a device for performing therapy on body tissue. The device includes a catheter, an end effector assembly connected to the catheter and configured to cauterize body tissue, an elongate member extending through the catheter and the end effector assembly and configured to move relative to the catheter and the end effector assembly, and a safety tip on the distal end of the elongate member configured to reduce damage to body tissue.

Another embodiment of the invention includes a device for performing therapy on body tissue. The device includes a catheter, an end effector assembly connected to the catheter and configured to cauterize tissue, wherein a port extends through the catheter and the end effector assembly, a needle extending through at least a portion of the port and configured to move relative to the port, and a cutter extending through at least a portion of the port and configured to move relative to the port.

A further embodiment of the invention includes a device for performing therapy on body tissue. A device includes a catheter, an end effector assembly connected to the catheter and configured to cauterize tissue, and a medical device extending through the catheter and the end effector assembly and configured to move relative to the catheter and the end effector assembly. The medical device is configured to deliver fluid, cut tissue, and cauterize tissue.

Various embodiments of the invention may have any or all of the following features. At least one of the elongate member and the safety tip may be configured to conduct electricity. At least one of the elongate member and the safety tip may be configured to cauterize body tissue. The end effector assembly may be configured to receive at least a portion of the safety tip. The elongate member may be configured to cut tissue. The device may include a port extending through the elongate member and the safety tip. The port may be configured to deliver fluid. The port may be configured to remove fluid. The elongate member may be a wire. The tissue cutting device may extend through the needle and may be configured to move relative to the needle. The device may include a safety tip connected to the end effector assembly and configured to reduce damage to body tissue. The device may include a second port extending through the end effector assembly. The port may be defined by a second catheter axially movable relative to the catheter and end effector assembly. The second catheter may define a second port. The medical device may be configured to conduct electricity. The medical device may define a first port and a second port. The first port may include a needle and the second port may be configured to deliver fluid. The needle may include a cutting mechanism extendable therefrom. The device may include a second medical device extending through the catheter and the end effector assembly and configured to move relative to the catheter and the end effector assembly.

Still another embodiment of the invention includes a method of performing therapy on body tissue. The method includes introducing a catheter into a gastrointestinal tract of a patient, advancing a distal end effector assembly of the catheter to tissue to be treated, the end effector assembly including an electrode assembly configured to cauterize tissue, and advancing a medical device through a lumen of the catheter, the medical device capable of delivering fluid, cutting tissue, and cauterizing tissue.

Various embodiments of the invention may have any or all of the following features. The medical device may be configured to conduct electricity. The method may include providing electricity to the electrode assembly. The method may include providing electricity to the medical device. The medical device may include a port. The method may include introducing fluid into the gastrointestinal tract via the port. The medical device may include a needle. The method may include advancing the needle into the tissue to be treated. A safety tip may be connected to the end effector assembly and configured to reduce damage to body tissue. The method may include moving the safety tip relative to the end effector assembly. The method may include advancing a second medical device through a second lumen of the catheter. The method may include moving the second medical device relative to the end effector assembly.

A still further embodiment of the invention includes a device for performing therapy on body tissue. The device may include a catheter, an electrically conductive elongate member extending through the catheter and configured to move relative to the catheter, and a safety tip on the distal end of the elongate member configured to reduce damage to body tissue.

Various embodiments of the invention may have any or all of the following features. The safety tip may be configured to conduct electricity. The elongate member may be configured cut tissue. The safety tip may be configured to cauterize tissue. The catheter may be made of an insulating material. A distal end of the catheter may be configured to conduct electricity. A distal end of the catheter may be configured to cauterize tissue. The safety tip may be made of an insulating material. A channel may extend through at least one of the catheter, the elongate member, and the safety tip. The channel may configured to deliver fluid. The channel may be configured to remove fluid. A plurality of channels may extend through the safety tip. A sheath may be disposed between the elongate member and the catheter. The sheath may be moveable relative to both the elongate member and the catheter.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2A is a perspective view of an endoscopic device according to another embodiment of the invention.

FIG. 3 is a perspective view of an endoscopic device according to a further embodiment of the invention.

FIG. 8 is a schematic view of an endoscopic device according to still another embodiment of the invention.

FIGS. 9A-9C are schematic views of an endoscopic device according to a still further embodiment of the invention.

FIGS. 11A-11B are schematic views of an endoscopic device according to yet another embodiment of the invention.

FIG. 20A is a schematic view of an endoscopic device according to a yet further embodiment of the invention.

FIG. 20B is a schematic view of an endoscopic device according to still another embodiment of the invention.

DESCRIPTION OF THE EMBODIMENTS

Reference will now be made in detail to the exemplary embodiments of the invention, examples of which are illustrated in the specification and accompanying drawings. Wherever possible, the same reference numbers will be used throughout the specification and drawings to refer to the same or like parts.

Figure 1A:
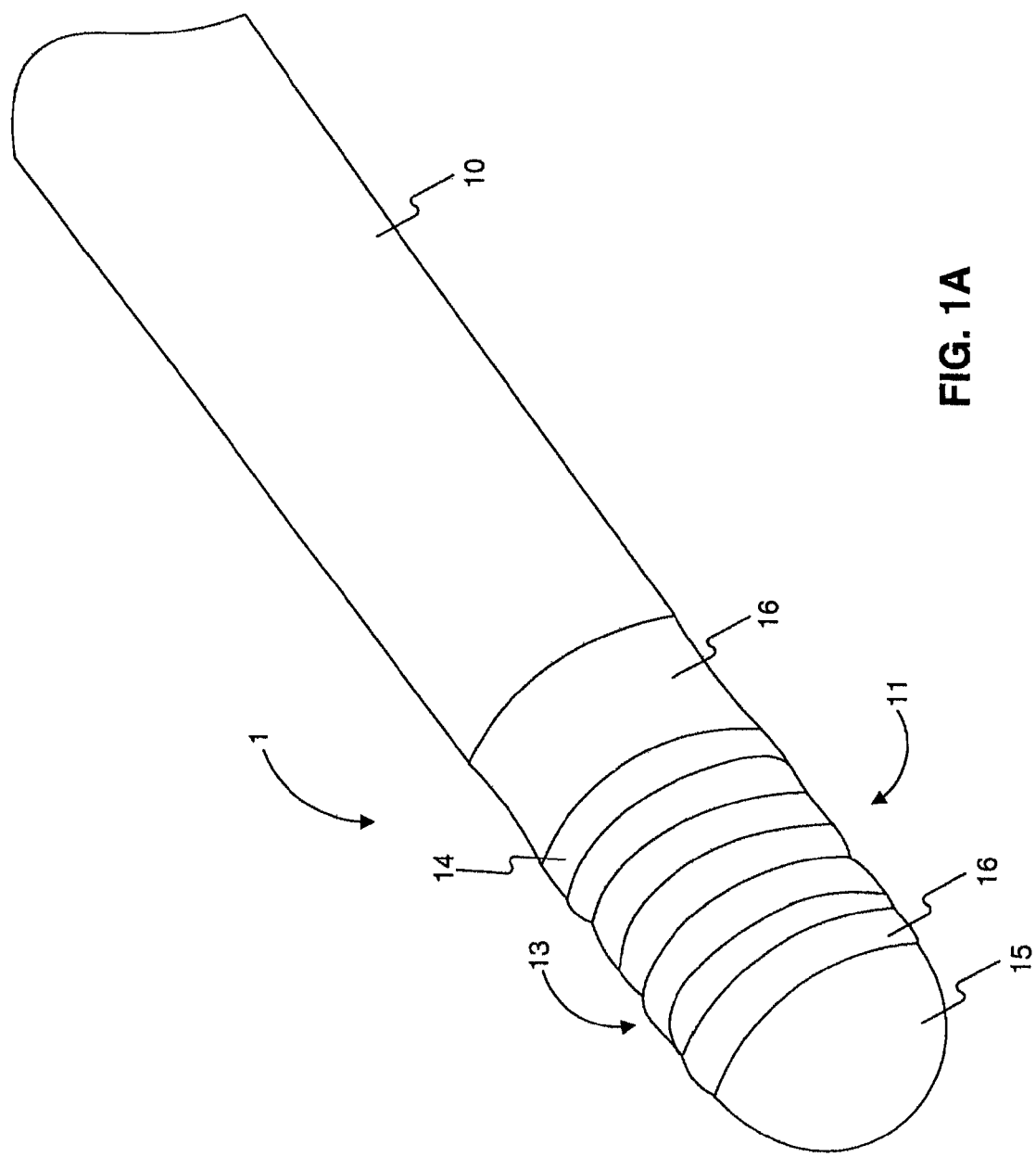
FIG. 1A is a perspective view of an endoscopic device according to an embodiment of the invention.
Figure 1B:
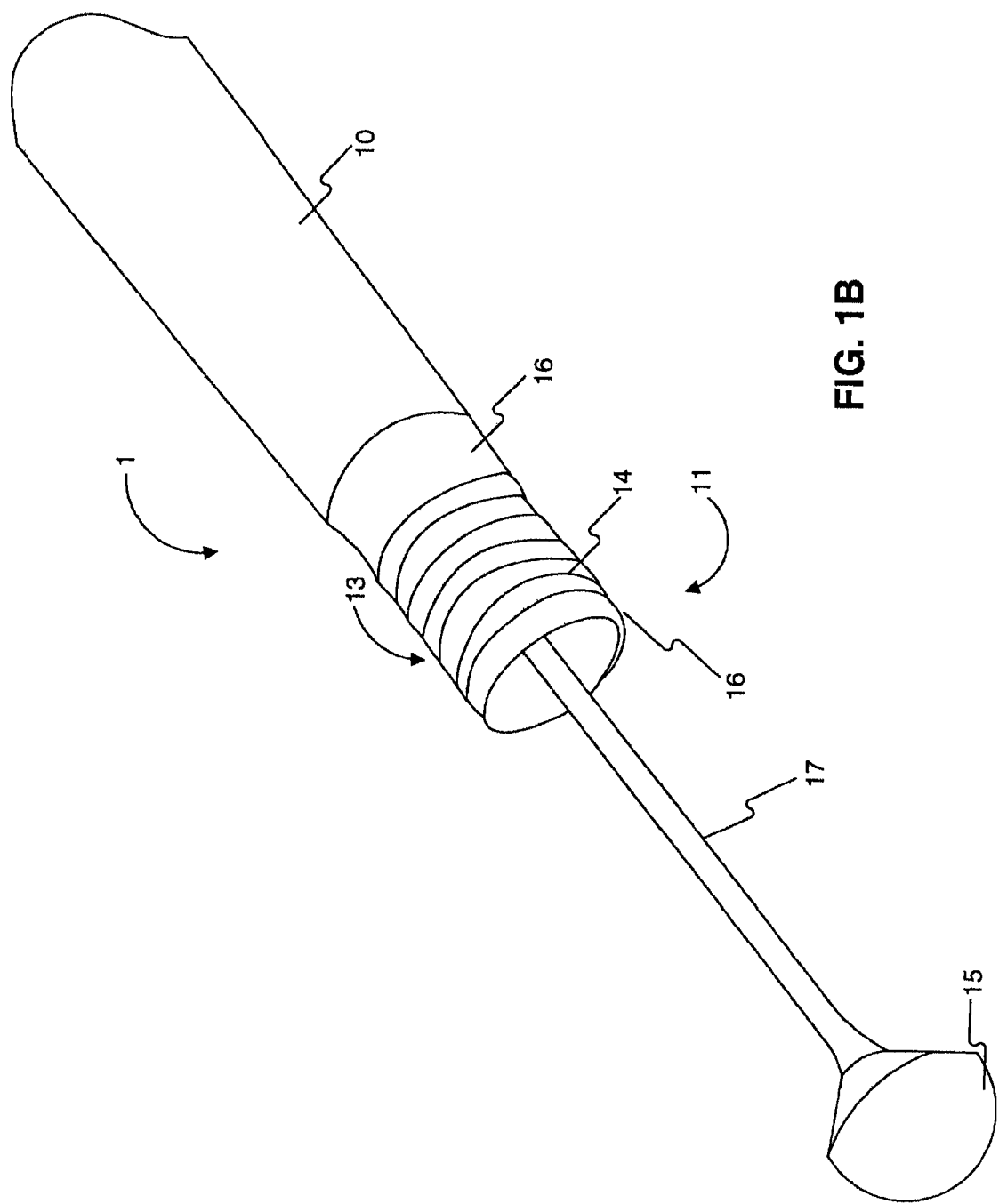
FIG. 1B is a perspective view of the endoscopic device of FIG. 1A in an alternate configuration.
Figure 6:
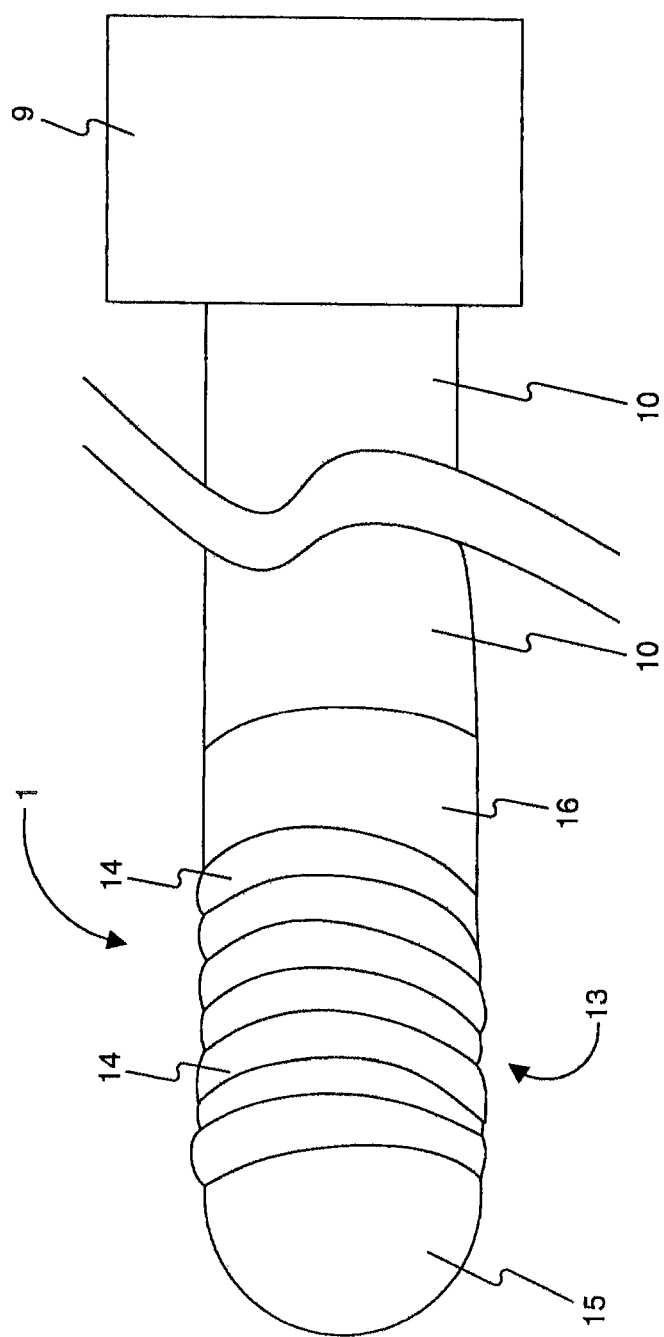
FIG. 6 is a schematic view of the endoscopic device of FIG. 1A.

FIGS. 1A-1B and 6 depict an exemplary embodiment of an endoscopic device. The endoscopic device may be used for endoscopic mucosal resection or other endoscopic procedures during which electrocautery and/or excising is desired. The endoscopic device 1 includes a catheter 10 with an end effector assembly 11 mounted on the distal end of the catheter 10. The catheter 10 is connected to a handle portion 9. Catheter 10 may be comprised of any suitable, elongate member known to one skilled in the art and having sufficient flexibility to traverse tortuous anatomy of a patient's gastrointestinal tract Catheter 10 defines a lumen therein.

Handle portion 9 similarly may be comprised of any suitable handle mechanism known to one skilled in the art and having the ability to control the operation of the endoscopic device 1 from outside of a patient. FIG. 6 depicts handle portion 9 in a general, non-specific form, as a box. However, the depiction of the handle portion in FIG. 6 as a box is exemplary only, as the handle portion 9 may be any type of suitable handle known in the art, examples of which are disclosed in U.S. Pat. Nos. 5,336,222, 5,403,311, 6,602,262 B2, 6,325,800 B1, and U.S. Patent Application No. 2002/0111623 A1, the entirety of all of which are incorporated herein by reference.

The end effector assembly 11 may include an electrode assembly 13. The end effector assembly 11 and any of its components may be controlled by handle portion 9 that connects to the end effector assembly 11 and its components via the catheter 10. The electrode assembly 13 may be either a monopolar or bipolar electrode assembly having a body portion 16 with one or more discrete spiral electrodes 14 disposed on the body portion 16. As shown in FIGS. 1A-6, 8, 9A-9C, 10A-10B, 11A-11B, 12A-12B, 13, 14A-14B, 15A-15N, 16A-16F, 17019, 20A-20b, 21, 22A-22B, and 23A-23B the body portion 16 may be cylindrical, however, the body portion 16 may have any desired geometric shape and/or configuration. The electrode assembly 13 may be connected via electrical leads to a power source, for example, a radio-frequency (RF) generator. An example of an electrode assembly, including a spherical distal tip, cylindrical body portion, discrete spiral electrodes, proximally extending shank, and electrical leads is disclosed in U.S. Pat. No. 5,336,222, the entirety of which is incorporated herein by reference. The electrode assembly 13 is configured to electro-coagulate tissue that comes into contact with a portion of the electrode assembly 13, for example, the one or more discrete spiral electrodes 14.

An elongate member 17 having a safety tip 15 may extend within the lumen of the catheter 10. When elongate member 17 is fully retracted within catheter 10, the safety tip 15 may be disposed on the distal end of the end effector assembly 11. The safety tip 15 is configured to prevent perforation of bodily tracts, for example the gastrointestinal tract, by portions of the end effector assembly 11 or elongate member 17.

The distal portion of the end effector assembly 11 is configured to receive, correspond to, and/or accommodate the proximal portion of the safety tip 15. For example, the safety tip 15 may have a substantially cone-shaped proximal portion. Correspondingly, the end effector assembly 11, and particularly its body portion 16, may have a substantially cone-shaped groove configured to receive the cone-shaped portion of the safety tip 15. The cone-shaped portion of the safety tip 15 and/or distal edge of the end effector assembly 11 (i.e., outer edge of the cone-shaped groove and/or body portion 16) may be arranged to cut and/or trap tissue, for example, while the cone-shaped portion of the safety tip 15 is being placed into the cone-shaped groove of the body portion 16. In the embodiment shown in FIGS. 1A-1B, the safety tip 15 has a substantially hemispherical configuration, however, any suitable shape and/or configuration is also contemplated, for example, round, triangular, oval, etc.

Figure 7N:
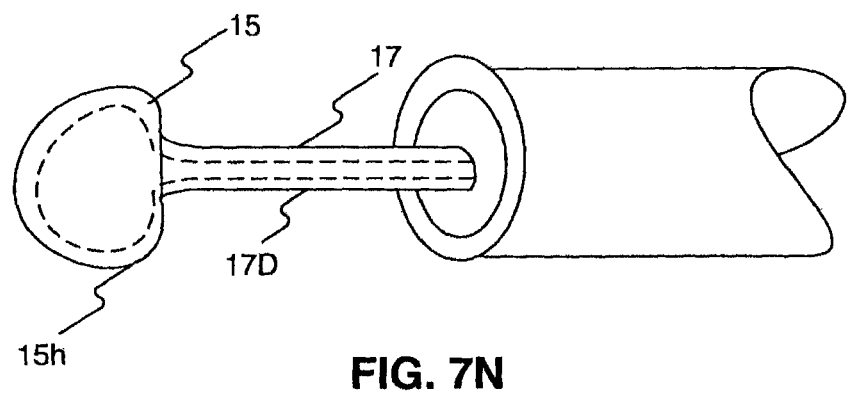
FIGS. 7A-7Q are schematic views of various safety tips according to various embodiments of the invention.
Figure 7O:
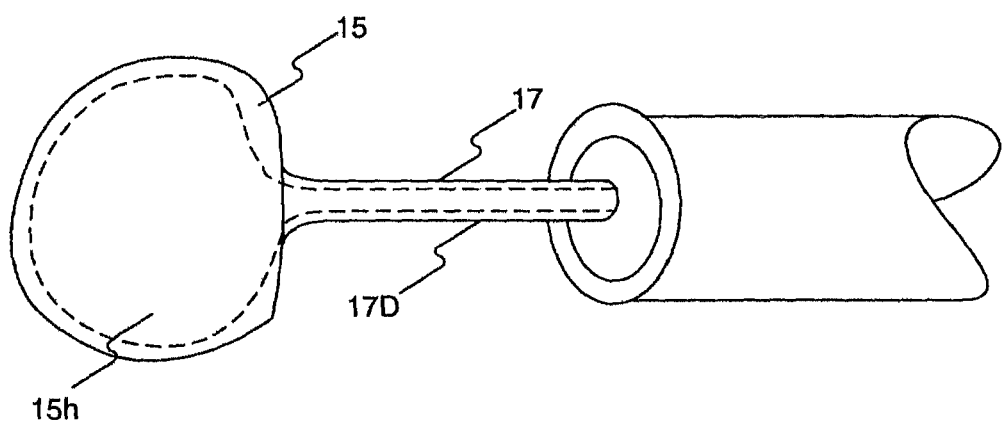
Figure 7P:
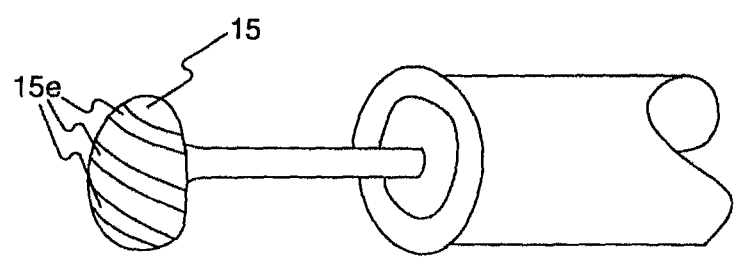
Figure 7Q:
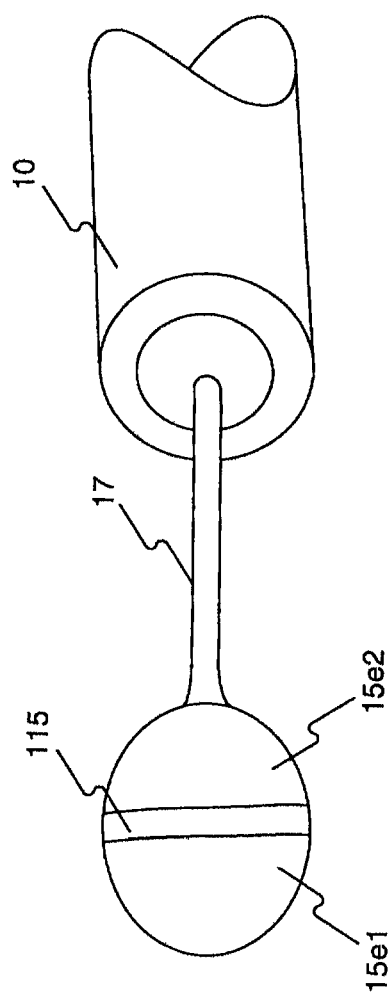

Non-limiting examples of safety tips 15 having various shapes and/or configurations are shown in FIGS. 7A-7Q. FIG. 7A depicts safety tip 15 having a substantially spherical configuration. Tip 15 in FIG. 7A may have any suitable diameter including any one of the following exemplary diameters: 2.0 mm; 1.85 mm; and 1.79 mm. FIG. 7B depicts safety tip 15 having a substantially conical configuration.

FIG. 7C depicts safety tip 15 having a pyramid-shaped configuration. FIG. 7D depicts safety tip 15 having a substantially conical configuration with the apex portion 15a of the conical-shaped safety tip 15 pointing away from elongate member 17, and a rounded configuration on the base portion 15b of safety tip 15 pointed toward and connected to elongate member 17. FIG. 7E depicts safety tip 15 having a pyramid-shaped configuration with the apex portion 15a of safety tip 15 pointing away from elongate member 17, and a rounded configuration on the base portion 15b of safety tip 15 pointed toward and/or connected to elongate member 17. FIG. 7F depicts safety tip 15 having a rounded configuration on the base portion 15a of safety tip 15 pointing away from elongate member 17, and a substantially conical configuration at the portion 15b of safety tip 15 pointing towards and connected to elongate member 17. FIG. 7G depicts safety tip 15 having a rounded configuration at the portion 15a of safety tip 15 pointing away from elongate member 17, and a pyramid-shaped configuration at the portion 15b of safety tip 15 pointing towards and connected to elongate member 17. FIG. 7H depicts safety tip 15 having a substantially teardrop-shaped configuration with safety tip 15 tapering toward elongate member 17. FIG. 7I depicts safety tip 15 having a substantially hemispherical configuration. FIG. 7J depicts safety tip 15 having a substantially hemispherical configuration at the portion 15a of safety tip 15 pointing away from elongate member 17, and a rounded configuration on the portion 15b of safety tip 15 pointed toward and connected to elongate member 17. FIG. 7K depicts safety tip 15 having a substantially elliptical configuration, with a major longitudinal axis 15x of safety tip 15 being disposed substantially perpendicular to elongate member 17. FIG. 7L depicts safety tip 15 having a substantially elliptical configuration, with a major longitudinal axis 15x of safety tip 15 being disposed substantially parallel to and/or coaxially aligned with elongate member 17. Tip 15 may rotate about member 17 via any suitable configuration, for example, a ball and socket assembly or a T and socket assembly.

FIG. 7M depicts safety tip 15 configured to rotate relative to elongate member 17, for example, about an axis 15x substantially perpendicular to elongate member 17. In this example, any suitable connection between member 17 and tip 15 that permits such rotational motion may be used, for example, by connecting member 17 to a stationary portion 15y, and having movable portion 15w rotate relative to stationary portion 15y. Such a configuration may reduce friction during cutting of tissue by member 17.

FIGS. 7N and 7O depict a safety tip 15 in an unexpanded and expanded configuration, respectively. Safety tip 15 may be made of an expandable material and may be expanded, for example, by placing a hollow interior 15h of safety tip 15 in flow communication with a source of fluid via a lumen 17l running through elongate member 17.

FIG. 7P depicts a bipolar safety tip 15 having one or more spirals 15e. One or more of spirals 15e may be electrodes and may be connected to the same power source, or may each be connected to different power sources.

Figure 21:
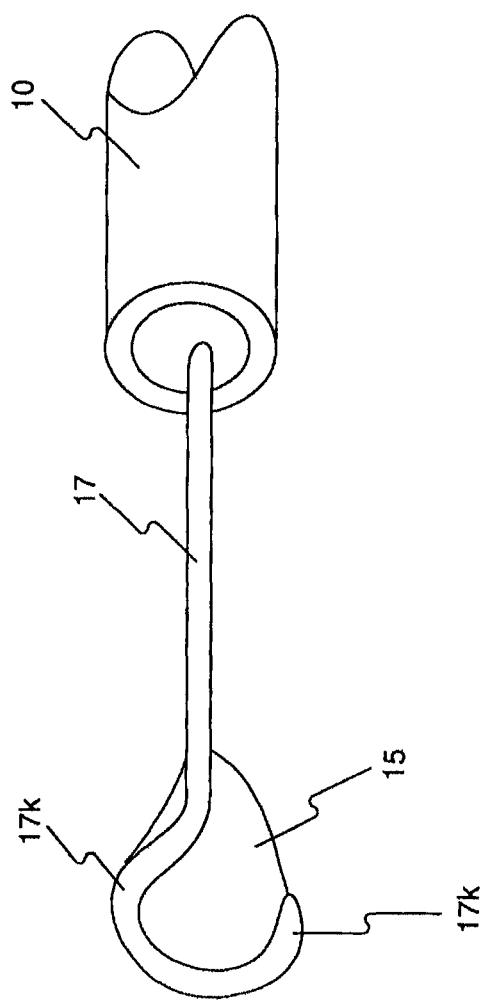
FIG. 21 is a schematic view of an endoscopic device according to a still further embodiment of the invention.

Safety tip 15 may be made out of any suitable material, for example, a conductive material such as stainless steel or a non-conductive such as ceramic. An example of a suitable material is Epoxy Tip Bipax Tra-Bond BA-FDA2T Lot 4030. Safety tip 15 may be placed on elongate member 17 using any method. For example, as shown in FIG. 21, an end 17k of elongate member 17 may have a substantially hook-like configuration and safety tip 15 may be formed around the substantially hook-like portion 17k of elongate member 17, for example, by injection molding or any other method.

The safety tip 15 is movable relative to the end effector assembly 11 and its electrode assembly 13 via elongate member 17. FIG. 1A shows the safety tip 15 in a retracted configuration, while FIG. 1B shows the safety tip 15 in an extended configuration. The safety tip 15 may be movable, for example, to reduce (and possibly prevent) the effect that the heat and/or energy from the electrode assembly 13, when activated, has on the safety tip 15. The safety tip 15 may be non-conductive so as to further reduce the effect of the electrode assembly 13 on the safety tip 15.

The safety tip 15 alternatively may be conductive and used as a cautery device to coagulate tissue that it may come into contact with. Such a conductive safety tip 15 may be electrically activated in conjunction with or separate from the electrode assembly 13, and may have either a monopolar or bipolar configuration. An example of a safety tip 15 having a bipolar configuration is shown in FIG. 7P. If conductive, the safety tip 15 may be electrically connected to a suitable power source known in the art (e.g., RF generator) via suitable electrical connections known in the art (e.g., electrical leads and/or wires or through member 17). The power source may be disposed anywhere on or relative to the device 1, for example, at the handle 9 or connected to the handle 9. Another example of a bipolar configuration is shown in FIG. 7Q, where electrodes 15e1 and 15e2 may be electrically isolated from each other by insulation 115, for example, such that they have opposite polarities.

Figure 13:
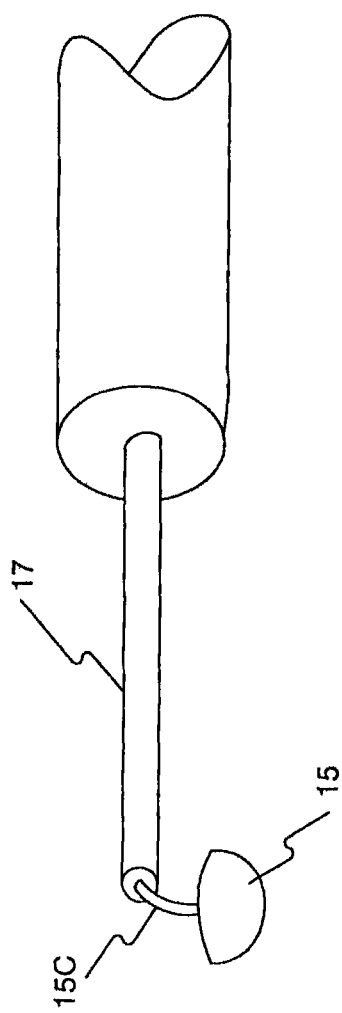
FIG. 13 is a schematic view of an endoscopic device according to still another embodiment of the invention.

Safety tip 15 may be movable relative to elongate member 17. For example, as shown in FIG. 13, safety tip 15 may be selectably detachable from elongate member 17, and may be connected to elongate member 17 via connector 15c in the detached configuration. Safety tip 15 may be detached from elongate member 17 to allow greater and/or more precise movement of elongate member 17. Connector 15c may be a flexible elongate member, such as a wire, that extends through member 17 and is controlled at handle 9. Connector 15c may move relative to member 17 within a lumen of member 17.

Figure 16A:
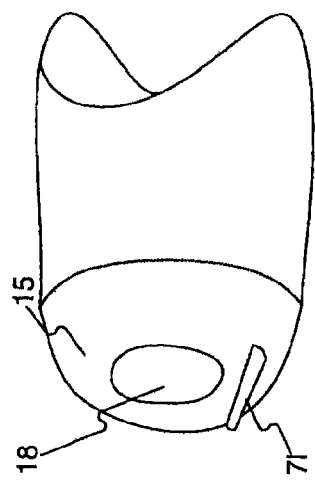
FIGS. 16A-16F are perspective views of various endoscopic devices according to various embodiments of the invention.

Safety tip 15 may have one or more cutting and/or cautery portions disposed thereon or relative to it. FIG. 16A depicts a safety tip 15 with a blade 70 extending from its distal end. Blade 70 may be selectively extended from and retracted within safety tip 15 and/or elongate member 17, for example, to prevent blade 70 from cutting tissue as safety tip 15 is advanced into a body lumen. In various embodiments, blade 70 may be in the shape of a triangle, cone, or any other shape, may be made of any suitable material, and/or may be configured to cauterize tissue (e.g., by being connected to a source of energy).

Figure 16B:
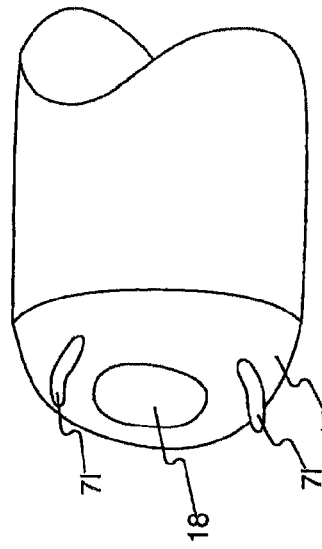

FIG. 16B depicts a safety tip 15 with a cautery portion 71 (e.g., a wire) disposed on a surface of safety tip 15 and/or offset from port 18. Cautery portion 71 may be configured to cauterize tissue and may be connected to a source of energy, for example, via a wire disposed in safety tip 15, elongate member 17, and/or another portion of device 1.

Figure 16C:
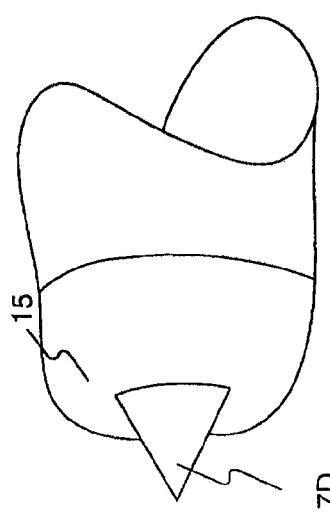
Figure 16D:
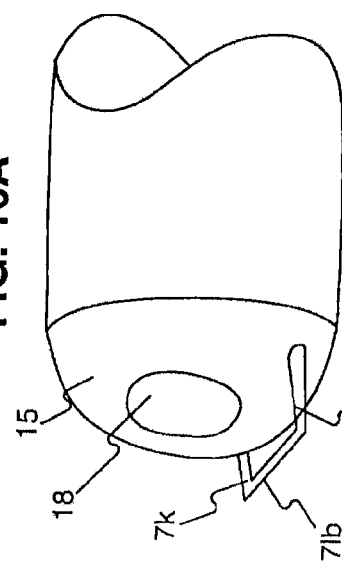

FIG. 16C depicts a safety tip 15 with a cautery portion 71 that extends from safety tip 15. In such a configuration, cautery portion 71 may include a portion 71a extending from a surface of safety tip 15, a portion 71b that is curved or bent relative to portion 71a and roughly follows the surface of safety tip 15, and a portion 71c that extends back towards the surface of safety tip 15. Both ends of cautery portion 71 (e.g., portions 71a, 71c) may be connected to and/or disposed within safety tip 15. Like blade 70, cautery portion 71 may be selectively extended from and retracted within safety tip 15 and/or elongate member 17, for example, to prevent cautery portion 71 from damaging tissue as safety tip 15 is advanced into a body lumen. For example, FIG. 16B may depict cautery portion 71 in the retracted configuration, and FIG. 16C may depict cautery portion 71 in the extended configuration. However, in various embodiments, blade 70 and/or cautery portion 71 may be disposed on any portion of safety tip 15 in any desired configuration. FIG. 16D depicts a safety tip 15 with a plurality of cautery portions 71.

Figure 16E:
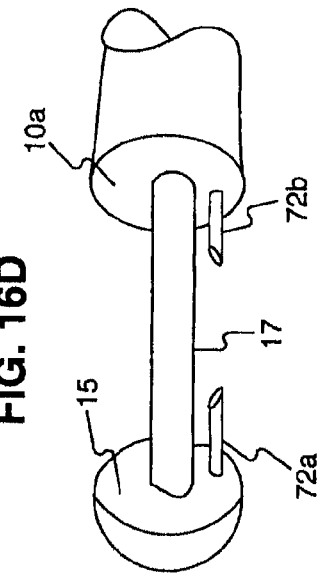
Figure 16F:
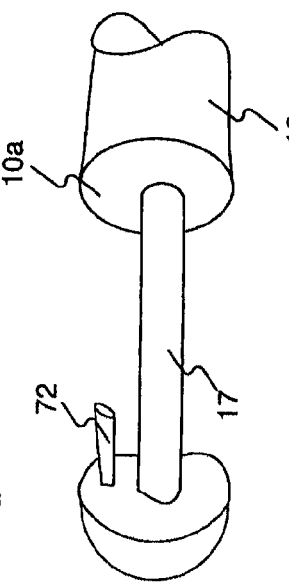

FIG. 16E depicts a safety tip 15 with a needle 72 extending toward catheter 10. In one example, catheter 10 may define a lumen or space configured to accommodate needle 72 when safety tip 15 is in a retracted configuration with respect to catheter 10. In another example, needle 72 may be selectably extended and/or retracted from safety tip 15 (e.g., needle 72 may be spring-loaded and/or needle 72 may be advanced through member 17 and/or safety tip 15, and may deflect backwards into safety tip 15 when needle 72 comes into contact with a distal end 10a of catheter 10). FIG. 16F depicts a device with one needle 72a, as shown in FIG. 16E, and another needle 72b disposed on catheter 10 and extending towards safety tip 15. Needles 72a, 72b may be selectably extended and/or retracted into safety tip 15 and catheter 10, respectively, using any suitable configuration, for example by being spring-loaded. In any such configuration, needles 72a, 72b may be configured to puncture tissue, but when needles 72a, 72b contact each other, they may be configured to retract into safety tip 15 and catheter 10, respectively. Needles 72a, 72b may be substantially coaxial and may be configured, for example, to deliver a cross-linking material (e.g., to treat hemostasis) to body tissue into which needles 72a, 72b have punctured from different directions (e.g., substantially opposite directions). In various embodiments, needle 72 may have any desired shape configured to puncture tissue (e.g., needle 72 may be tapered and may be curved), may be configured to deliver any fluid set forth herein into any body cavity and/or body tissue, and/or may be connected to a fluid source via a lumen extending through any portion of device 1, for example, safety tip 15, elongate member 17, and/or catheter 10. Moreover, needles 72 may be each be connected to substantially the same fluid source, or needle 72a may be connected to a first fluid source, while needle 72b is connected to a second fluid source different from the first fluid source. Furthermore, needles 72 may each be configured to deliver substantially the same fluid, or needle 72a may be configured to deliver a first fluid while needle 72b may be configured to deliver a second fluid different from the first fluid. Additionally, needles 72 may be configured to deliver the fluid or fluids at substantially the same time, or needle 72a may be configured to deliver fluids at a time different from needle 72b.

The elongate member 17 may be configured to be a cutting wire 17, for example, to cut away tissue from within the gastrointestinal tract. The cutting wire 17 may be sufficiently thin and therefore sharp that the cutting wire 17 cuts tissue when brought into contact with and/or moved relative to the desired tissue. The cutting wire 17 may be electrically active (having either a monopolar or bipolar configuration) so as to assist in cutting tissue. If conductive, the cutting wire 17 may be electrically connected to a suitable power source known in the art (e.g., RF generator) via suitable electrical connections known in the art (e.g., electrical leads and/or wires). The power source may be disposed anywhere on or relative to the device 1, for example, at or connected to the handle 9.

Elongate member 17 may have any desired dimensions. For example, elongate member 17 may have any suitable diameter, including diameters of approximately 0.015 inches and approximately 0.01 inches. In another example, elongate member 17 may have any suitable length between the distal end of catheter 10 and safety tip 15, including lengths of approximately 4.00 mm. Elongate member 17 may also be made of any suitable material. For example, elongate member 17 may be made of stainless steel.

The elongate member 17 may be eccentrically located and/or configured to bend, for example, with respect to the longitudinal axis of the device 1. Such eccentric location and/or bending of the elongate member 17 may assist various portions of the device 1 (e.g., the elongate member 17 and/or safety tip 15) in cutting and/or coagulating tissue.

Figure 9C:
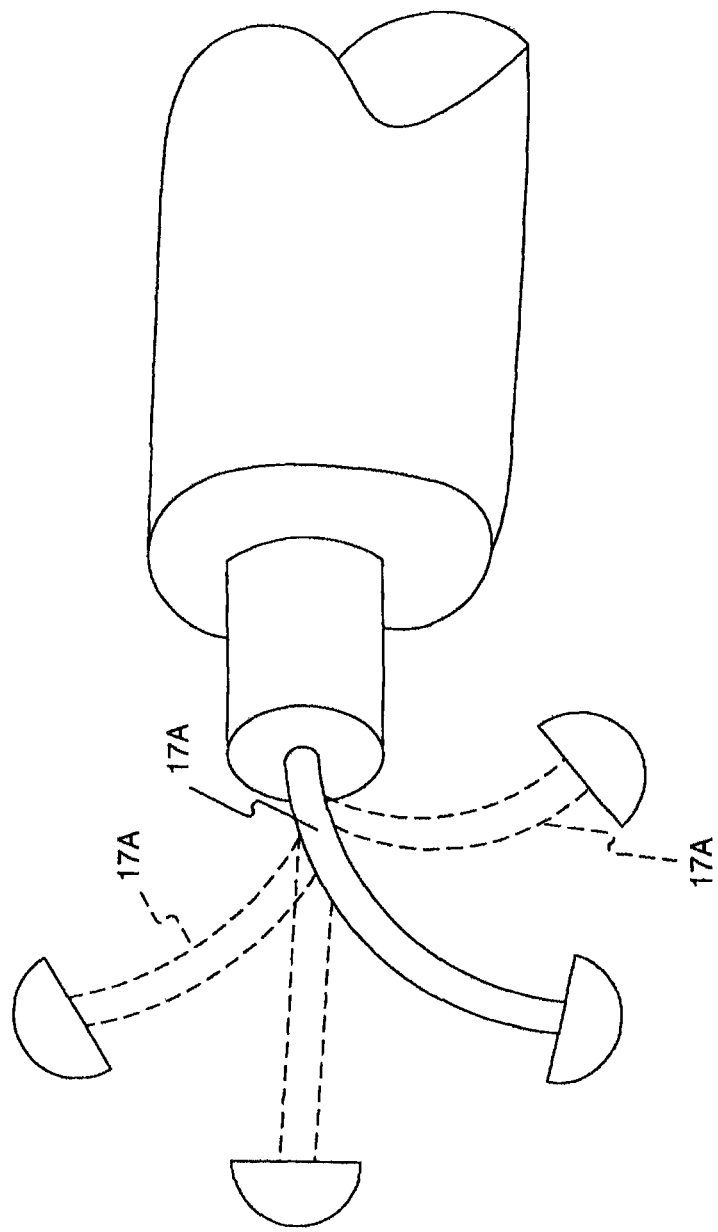

For example, as shown in FIGS. 9A and 9B, a portion 17a of elongate member 17 may be configured to curve when elongate member 17 is extended from catheter 10. Portion 17a may curve as shown in FIG. 9B because it is made of a material configured to receive and hold a preformed curve, for example, nitinol. Such material that makes up portion 17a may be substantially the same as or different from the material that makes up other portions of elongate member 17. As shown in FIG. 9C, however, such portion 17a may be selectably curvable and/or rotatable so as to allow the user to control the direction and extent of curvature of portion 17a. Any suitable mechanism at handle 9 to control the curvature and rotational orientation of portion 17a may be used, for example, a free swivel type device that allows member 17 to self-orient according to the curvature of and/or force applied to member 17, or a screw mechanism used to control rotatable endoscopic devices such as snares. An example of such a screw mechanism is an internal and distally placed screw mechanism, such as that disclosed in U.S. Pat. No. 6,602,262, the entirety of which is incorporated herein by reference.

Figure 12A:
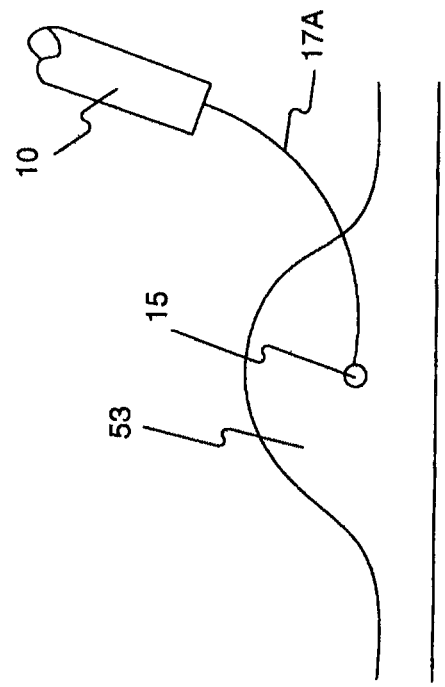
FIG. 12A is a schematic view of a method of using the endoscopic device of FIG. 1B.
Figure 12B:
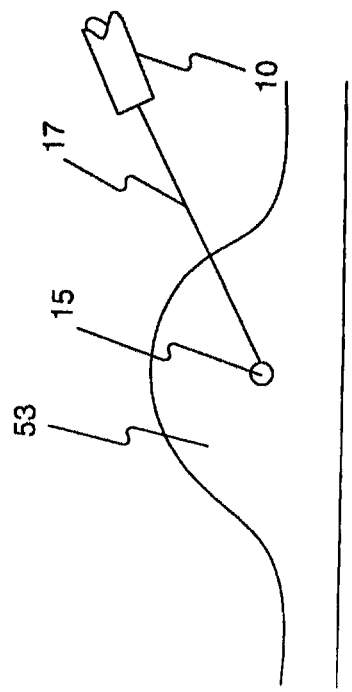
FIG. 12B is a schematic view of a method of using the endoscopic device of FIGS. 9A-9C.

Such an elongate member 17 having a curved portion 17a may be desirable, for example, to allow a user greater control of a cutting instrument (e.g., the elongate member 17) and/or to remove greater amounts of a lesion 53 (see FIGS. 12A-12B) than could otherwise be done with a straight elongate member 17. Such an advantage is illustrated in FIGS. 12A and 12B, where elongate member 17 having curved portion 17a in FIG. 12B is configured and positioned to remove a greater volume of lesion 53 than straight elongate member 17 of FIG. 12A.

Figure 15H:
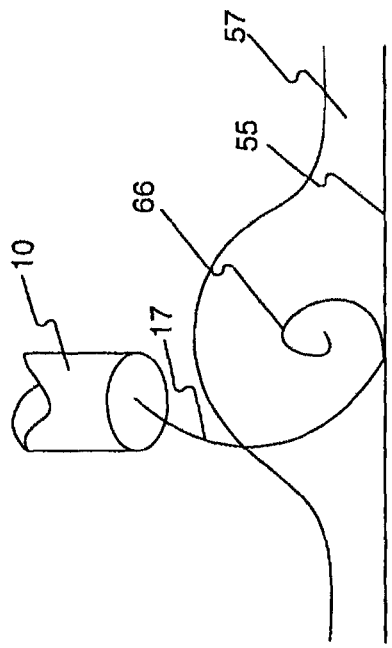
FIGS. 15A-15N are schematic views of various elongate members according to various embodiments of the invention.
Figure 15J:
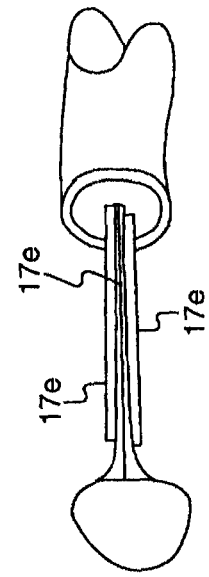
Figure 15L:
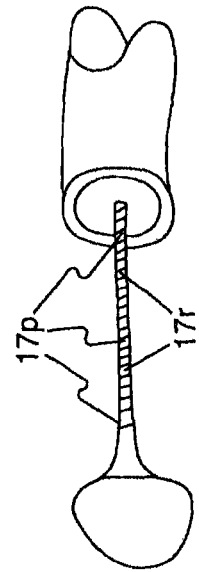
Figure 15G:
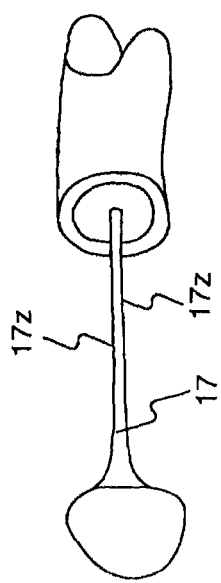
Figure 15I:
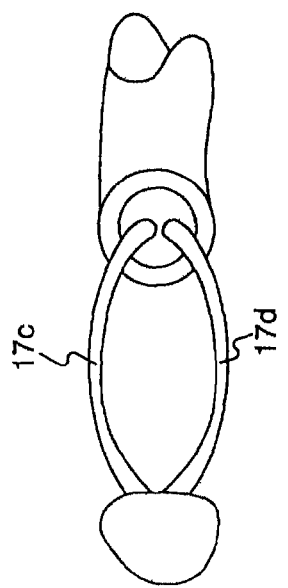
Figure 15K:
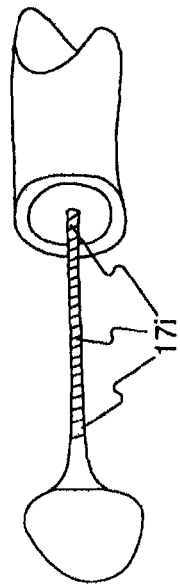
Figure 15N:
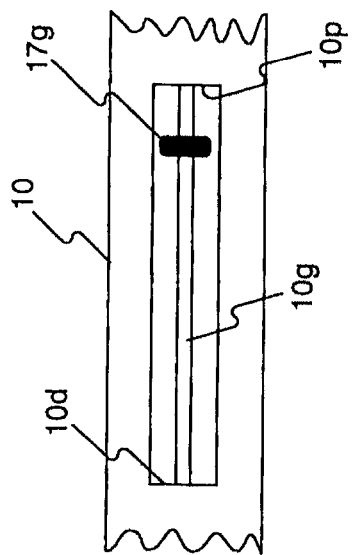

Elongate member 17 may have any suitable shape and/or configuration, and may have any number of various components, some examples of which are shown in FIGS. 15A-15N. FIG. 15A depicts an elongate member 17 having a bow portion 60 whose ends 60a, 60b are connected to elongate member 17, and whose central portion 60c is disposed away from elongate member 17. FIG. 15B depicts an elongate member 17 that has a bowed portion 17b offset from a longitudinal axis 17x of the rest of the device.

FIG. 15C depicts an elongate member 17 having a slotted portion 61 at an end of member 17 that extends from catheter 10. Slotted portion 61 may be configured to receive, for example, a blade or other flat and/or thin object to perform an operation on the body. Such an object may slide within slot 61 and connect to the handle 9 by an actuator through member 17 and/or catheter 10.

FIG. 15D depicts an elongate member 17 having a hoop-like portion 62 defining a hole 62a. FIG. 15E depicts an elongate member 17 having a groove 63 configured to guide a tool 65 or other object along elongate member 17. Elongate member 17 may also include a ramp and/or elevator portion 64 disposed on an end of groove 63 that is configured to deflect a tool 65 or other object away from elongate member 17.

FIGS. 15F and 15G depict an elongate member 17 having a blade-like configuration. For example, elongate member 17 may have one or more edges 17z that may be relatively sharp, for example, to be configured to cut tissue. In cross-section, elongate member 17 may have any suitable shape or configuration, for example, a substantially triangular configuration (e.g., as shown in FIG. 15F), pie-shaped configuration, teardrop-shaped configuration, and/or substantially flat configuration (e.g., as shown in FIG. 15G).

FIG. 15H depicts an elongate member 17 having an end 66 in a floppy or J-shaped configuration. End 66 may be configured to prevent unintended perforation of tissue 55 (e.g., the esophagus) by end 66 when elongate member 17 is advanced into a body cavity 57.

FIG. 15I depicts an elongate member 17 that includes two elongate members 17c, 17d that are configured to cooperate with each other, for example, so as to act like a snare configured to surround and sever lesions, polyps, or other tissue. Members 17c, 17d each may assume a preformed configuration shown in FIG. 15I when members 17c, 17d extend from catheter 10.

FIG. 15J depicts an elongate member 17 including one or more stiffening members 17e (e.g., stiffening mandrel or hypotube), for example, configured to assist in maintaining a desired curvature (or lack thereof) of elongate member 17.

FIG. 15K depicts an elongate member 17 including indicators 17i (e.g., striations, markers) configured to allow a user to visually ascertain the position of elongate member 17 relative to other objects, for example, to ascertain the size of a tissue to be cut and/or to ascertain how much of elongate member 17 has been extended past the distal end of catheter 10. Indicators 17i may be viewed with an endoscope or any other suitable visualization method, including fluoroscopy.

FIG. 15L depicts an elongate member 17 configured to provide bipolar cautery, for example, via electrode pairs 17p and 17r. Pairs 17p, 17r may be spiral-shaped and may be connected to a source of bipolar cautery current by any suitable connection means.

Figure 15M:
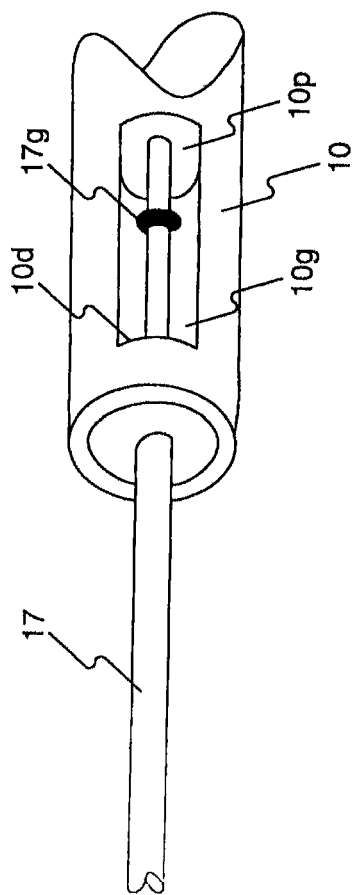

FIGS. 15M and 15N depict an elongate member 17 including one or more stops 17s configured, for example, to constrain movement of elongate member 17 in a proximal and/or distal direction. For example, stop 17s may be rigidly connected to elongate member 17 and may be disposed within slide area 10s of catheter 10. Accordingly, stop 17s is configured to move within slide area 10s, but once stop 17s comes into contact with proximal end 10p or distal 10d of slide area 10s, stop 17s prevents elongate member 17 from moving proximally and/or distally relative to catheter 10.

Figure 17:
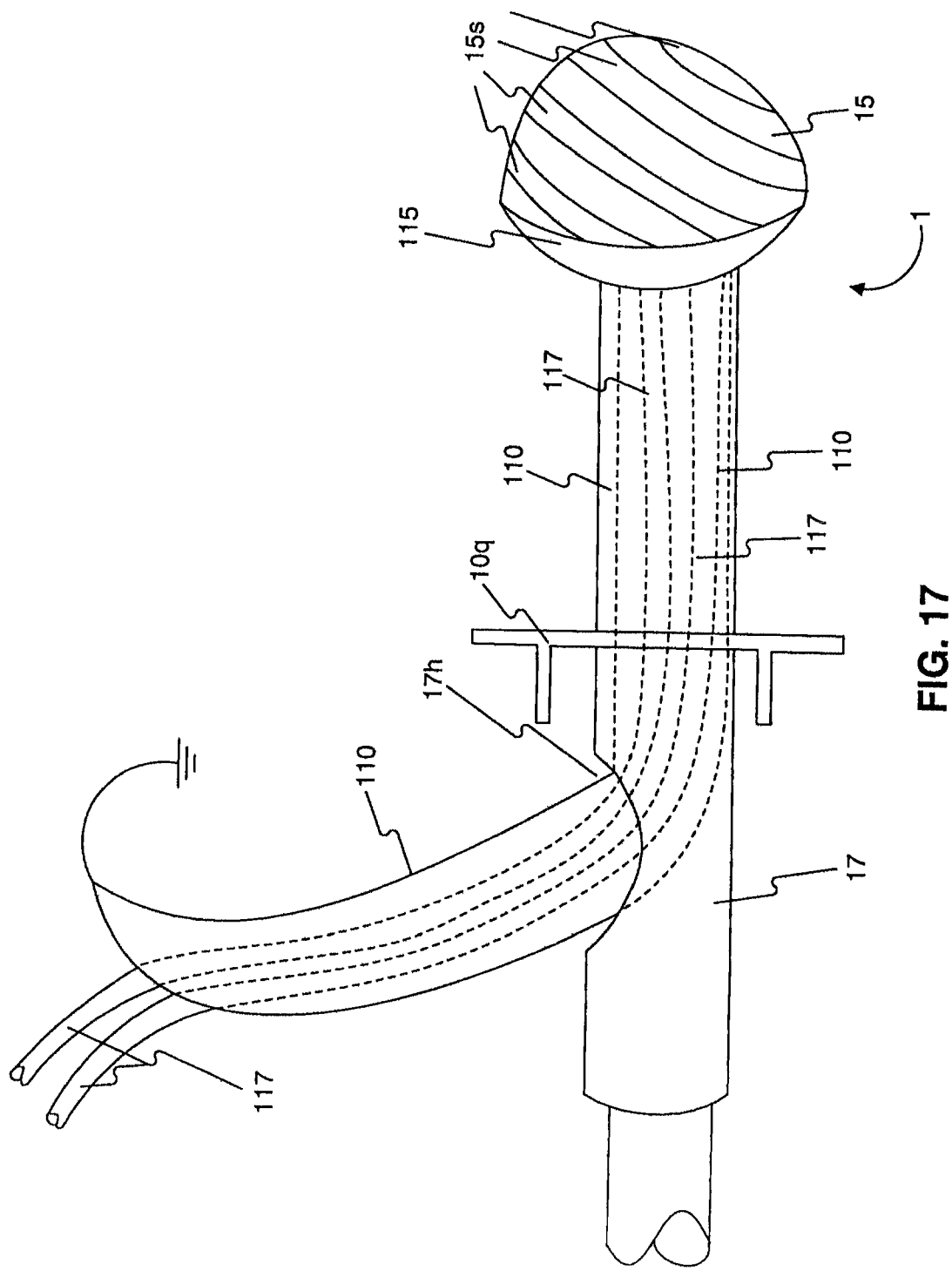
FIG. 17 is a schematic view of an endoscopic device according to another embodiment of the invention.

Elongate member 17 and safety tip 15 may be independently connected to one or more sources of power, for example, to assist in cutting and/or cauterizing tissue. For example, as shown in FIG. 17, device 1 may include a monopolar elongate member 17 and a bipolar safety tip 15. Member 17 may extend through a distal portion 10q of a catheter. Monopolar elongate member 17 may be connected to a source of current at its proximal end. Bipolar safety tip 15 may be insulated from monopolar elongate member 17 by insulation 115, and may be connected by one or more wires 117 to one or more sources of energy, such as RF energy. Wires 117 may each be independently connected to different spiral electrodes 15s of safety tip 15. Spirals 15s may be electrically insulated from each other, and may each be configured to cauterize tissue. Wires 117 may be disposed within insulation 110 and all of wires 117 and insulation 110 may extend through at least a portion of elongate member 17. A hole 17h in elongate member 17 may be configured to allow wires 117 and insulation 110 to extend out of elongate member 17. Insulation 110 may be grounded, for example, at its proximal end. Accordingly, in such a configuration, an electrical system including bipolar safety tip 15 and wires 117 may be substantially electrically isolated from another electrical system including monopolar elongate member 17 via one or more of insulation 110 and insulation 115, such that each electrical system may be operated independently of the other.

The elongate member 17 may have one or more endoscopic tools deployed with and/or on the elongate member 17. The one or more endoscopic tools may be disposed within the end effector assembly 11 when the safety tip 15 and/or elongate member 17 is in the retracted configuration, for example, by occupying the space within the end effector assembly 11 substantially adjacent to the elongate member 17. For example, a hook-like cutting wire may extend from a side portion of elongate member 17. In another example, a snare may be attached to the elongate member 17.

The endoscopic device 1, including its catheter 10, end effector assembly 11, safety tip 15, and/or elongate member 17, may have one or more ports and/or channels. The port(s) and channel(s) may be configured to perform any endoscopic function and/or accommodate any endoscopic device.

Figure 2B:
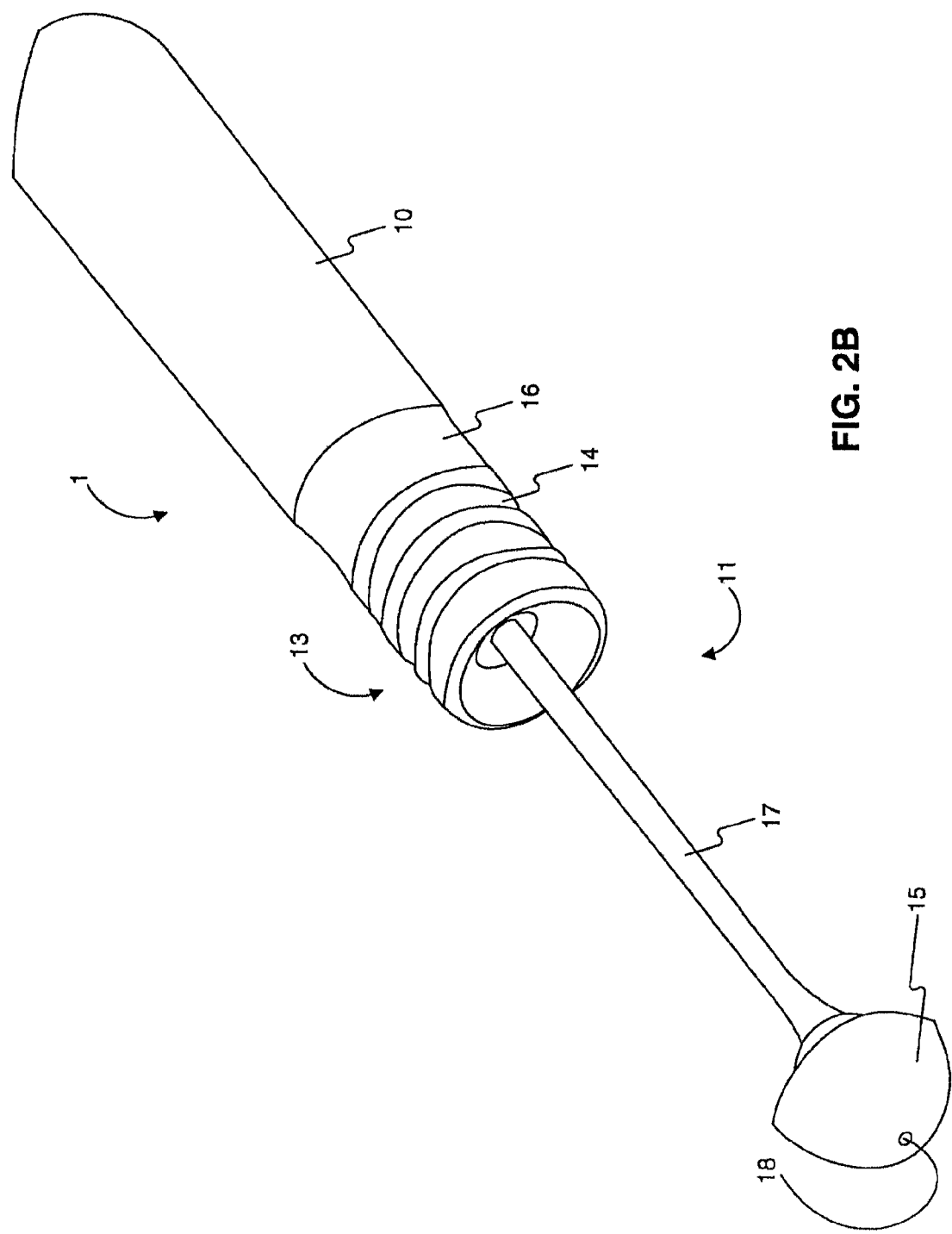
FIG. 2B is a perspective view of the endoscopic device of FIG. 2A in an alternate configuration.

For example, in the embodiment shown in FIGS. 2A and 2B, the safety tip 15 and elongate member 17 may have a port 18 in flow communication with a channel 18a configured to introduce materials (e.g., gas(es), fluid(s), solid(s), or any combination of any of these elements) into the gastrointestinal tract or any other desired body portion, for example, between submuscosa tissue layers of the gastrointestinal tract so as to separate the mucosal tissue layer from the muscularis layer. The embodiment therefore may be used in any endoscopic procedure during which electrocautery, excising, and/or injection is desired, without the need for an exchange of catheters. The channel 18a may extend through the safety tip 15 and member 17 to a fluid or solid source connected to a proximal end of member 17. The port 18 and/or channel 18a may be configured to introduce fluid and/or solids into the gastrointestinal tract when the safety tip 15 is in the extended and/or retracted configuration relative to the end effector assembly 11. Some examples of materials (e.g., gas(es), fluid(s), solid(s), or any combination of any of these elements) that may be introduced using the port 18 and/or channel 18a include agents to stain or dye tissue, for example for lesion identification, anticholinergic agents for peristalsis inhibition, sclerotic agents for enhancing electro-coagulation of the tissue, vaso-constrictor drugs, flushing fluids, cross-linking agents for treating hemostasis, and/or any other agent, fluid, drug, or solid known in the art and suitable for an endoscopic procedure. The port 18 and/or channel 18a may also and/or alternatively be configured to remove materials from the gastrointestinal tract or any other desired body portion, for example, through the use of suction.

In some embodiments, the port 18 and/or channel 18a may also be configured to accommodate one or more endoscopic tools therethrough, whether or not the safety tip 15 and/or elongate member 17 are in the extended or retracted position relative to the end effector assembly 11 and/or electrode assembly 13. Examples of endoscopic tools that may be used in conjunction with this embodiment include a cutting wire, an injection needle, a needle knife, a snare, or other therapeutic or diagnostic devices, including any of the exemplary devices set forth herein. The port 18 and/or channel 18*a* may be configured to irrigate materials into and/or aspirate materials from the gastrointestinal tract even with an endoscopic tool extending therethrough. For example, the port 18 and/or channel 18*a* may have a cross-sectional area larger than a cross-sectional area of the endoscopic tool extending therethrough. In another example, the port 18 and/or channel 18*a* may have a cross-sectional geometric shape that allows materials to be irrigated to and/or aspirated from the gastrointestinal tract even with the endoscopic tool extending therethrough (e.g., the cross-section of the port 18 is square, while the cross-section of the endoscopic tool is round).

As shown in FIG. 8, the distal end of safety tip 15 may include a plurality of ports 18*a*. Each of the plurality of ports 18 may connect to one or more channels 18*a* that extend through elongate member 17 and/or any other portion of endoscopic device 1. Each of ports 18 may be in fluid communication with the same channel 18*a*, or one or more ports 18 may be in fluid communication with its own dedicated, respective channel 18*a*. One or more of the plurality of ports 18, and its channel 18*a*, may be configured to perform substantially the same function (e.g., remove materials from the gastrointestinal tract) or they may each be configured to perform different functions (e.g., introduce solids and/or fluids into the gastrointestinal tract while other ports 18 and channels 18*a* may be configured to remove materials from the gastrointestinal tract). Ports 18 and corresponding channels 18*a* may be used to introduce multiple tools to the treatment site.

Figure 10A:
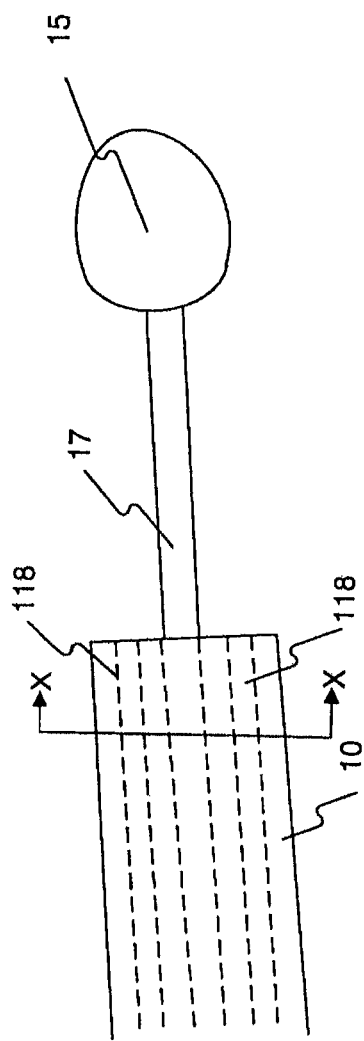
FIG. 10A is a schematic view of an endoscopic device according to a further embodiment of the invention.
Figure 10B:
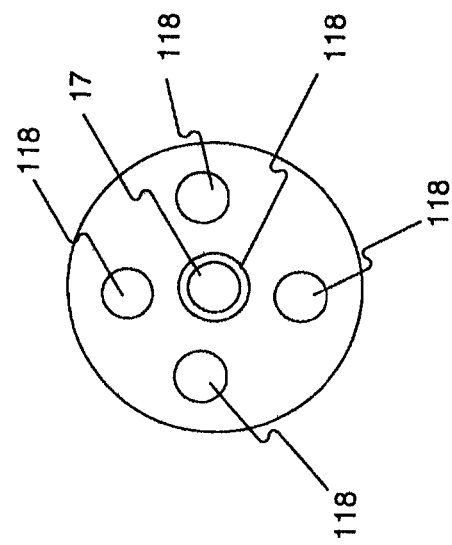
FIG. 10B is a cross-sectional view of the endoscopic device of FIG. 10A along line X-X of FIG. 10A.

Ports 18 and/or channel 18*a* may be disposed relative to any component of device 1 in any configuration. For example, as shown in FIGS. 2A-2B, 3, 14A-14D, and 16B-16D, port 18 and/or channel 18*a* may be disposed within safety tip 15 and elongate member 17, and may be substantially coaxial with a longitudinal axis of one or more of safety tip 15, elongate member 17, and catheter 10. In another example, as shown in FIG. 8, ports 18 and corresponding channels 18*a* may be disposed within safety tip 15, and may be variably offset from a longitudinal axis of one or more of safety tip 15, elongate member 17, and catheter 10. As shown in FIGS. 10A and 10B, one or more ports 118 and/or channels 118 may be disposed within catheter 10 as opposed to safety tip 15 and/or elongate member 17. Channels 118 may run substantially parallel to elongate member 17 and/or the channel 118 within which elongate member 17 is disposed in catheter 10.

Figure 14B:
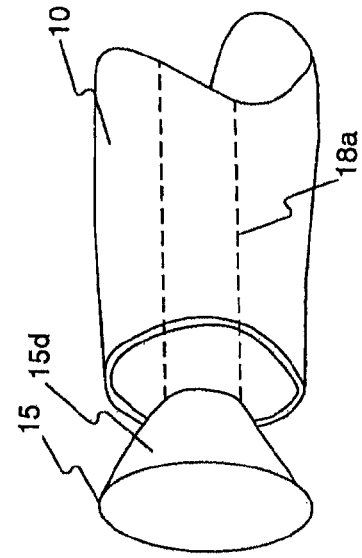
FIGS. 14A-14D are schematic views of an endoscopic device according to a still further embodiment of the invention.
Figure 14D:
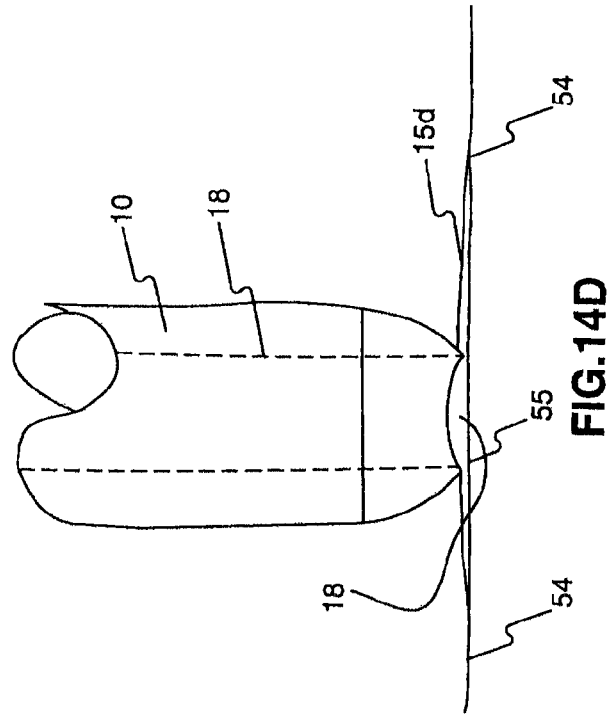
Figure 14A:
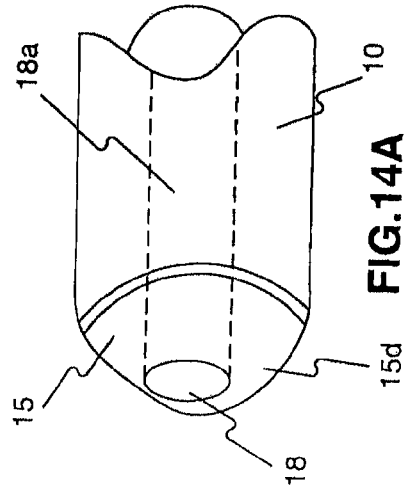
Figure 14C:
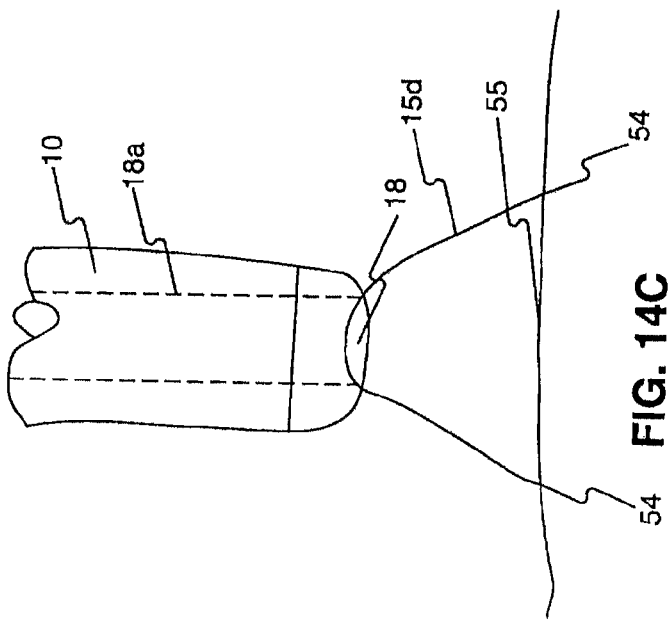

A flexible head 15*d* may be defined by safety tip 15 and/or may be connected to safety tip 15, for example, where safety tip 15 meets port 18. Flexible head 15*d* may be made out of any material, for example, an airtight material configured to reverse or invert upon actuation and may be configured to accommodate suction and/or a vacuum. In a first configuration, as shown in FIG. 14A, flexible head 15*d* may define and/or be substantially flush with the surface of safety tip 15. In a second configuration, as shown in FIG. 14B, covering 15*d* may invert and extend distally away from catheter 10 and/or the surface of safety tip 15. Flexible head 15*d* may be extended and/or actuated using any method. In the second configuration, covering 15*d* may be configured to create a vacuum chamber in conjunction with suction from port 18. Thus, covering 15*d* may assist in funneling fluid and/or debris from a body cavity into port 18. In another example, however, as shown in FIG. 14C, edge 54 of flexible head 15*d* may be pressed against tissue surface 55 so as impede airflow into air chamber 56 defined by flexible head 15*d* and tissue surface 55. Suction may then be initiated through port 18 such that air is substantially removed from air chamber 56 and at least a portion of flexible head 15*d* is substantially flush with tissue surface 55, for example, as shown in FIG. 14D.

In another embodiment of a device according to the invention, and shown in FIG. 3, a device 19 includes a safety tip 15' having a port 20 configured to accommodate an endoscopic tool therethrough. In this embodiment, the safety tip 15' is fixed to and/or integrally formed with the end effector assembly 11 and is not connected to an elongate portion 17. The port 20 may extend through at least portions of the safety tip 15', the end effector assembly 11 and its electrode assembly 13, and the catheter 10. One or more endoscopic tools may extend through port 20. Examples of endoscopic tools that may be used in conjunction with this embodiment include a cutting wire, an injection needle, a needle knife, a snare, or other therapeutic or diagnostic devices, including any of the exemplary devices set forth herein.

Figure 4:
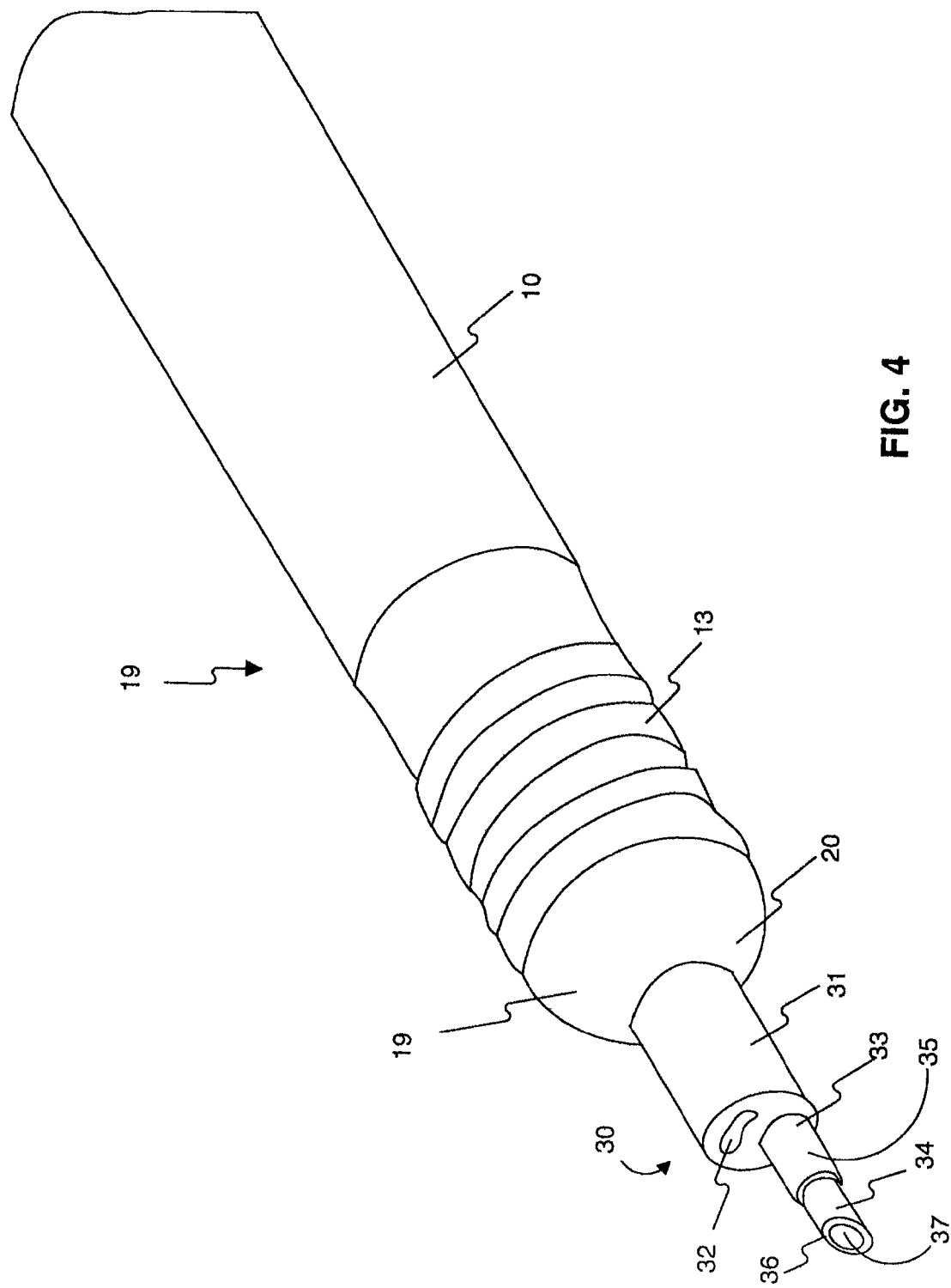
FIG. 4 is a perspective view of an endoscopic device according to yet another embodiment of the invention.

An example of an endoscopic tool that may be used with the endoscopic device 19 having a channel 20 is depicted in FIG. 4. The endoscopic tool 30 has an elongate housing 31, such as a catheter, that may have one or more elongate channels extending therethrough. In this embodiment, the elongate housing 31 has two elongate channels 32, 33 that are substantially coaxial with each other and the elongate housing 31. The elongate channels 32, 33 in FIG. 4 have different cross-sectional shapes, however, they may have the same cross-sectional shape. One of the channels 32 may be configured to introduce materials into the gastrointestinal tract, for example, to flush the portion of the gastrointestinal tract where therapy is being performed. The other channel 33 may be configured to accommodate an injection needle 34, a snare, or any other endoscopic tool and/or allow the injection needle 34, the snare, or other endoscopic tool to move axially relative to the elongate housing 31.

The injection needle 34 may have an outer sheath covering 35 disposed around and axially movable relative to the injection needle 34. In the position shown in FIG. 4, the distal end of sheath 35 is proximal to a sharpened portion 36 of the needle 34. The injection needle 34 may be configured to penetrate tissue, for example, by having a sharpened portion 36 that is angled relative to the longitudinal axis of the injection needle 34. The needle 34 may also be used to introduce materials into the gastrointestinal tract or any other body portion through its lumen 37. The needle 34 may be electrically active (i.e., monopolar or bipolar) so as to penetrate tissue and/or assist in penetrating tissue.

The sheath 35, or any other endoscopic tool, sheath, or lumen on or used in conjunction with endoscopic tool 30, may be electrically active (i.e., monopolar or bipolar). The sheath 35 may be configured to create a vacuum and/or introduce materials into the gastrointestinal tract and/or tissue defining the gastrointestinal tract. The creation of the vacuum and/or introduction of materials may be implemented around an endoscopic tool extending through the sheath 35, or separate from the endoscopic tool as the endoscopic tool does not extend through the sheath 35. For example, the sheath 35 may be configured to create a vacuum so as to position tissue (e.g., place tissue in the sheath 35), and then the needle 34 may be advanced through the sheath 35 and into the tissue.

Some or all of the electrode assembly 13, the safety tip 15', the elongate housing 31, the injection needle 34, the outer covering 35, and any other portion of device 19 may be configured to move axially or otherwise relative to each other, for example, by being made of either different or same materials suitable for such movement and/or having dimensions that allow the aforementioned portions to move relative to each other. Thus, the injection needle 34 may be retracted inside the outer covering 35, the outer covering 35 may be retracted inside port 33 of the outer housing 31, and/or outer housing 31 may be retractable inside safety tip 15', electrode assembly 13, catheter 10, and/or any other portion of the device 1.

Figure 5:
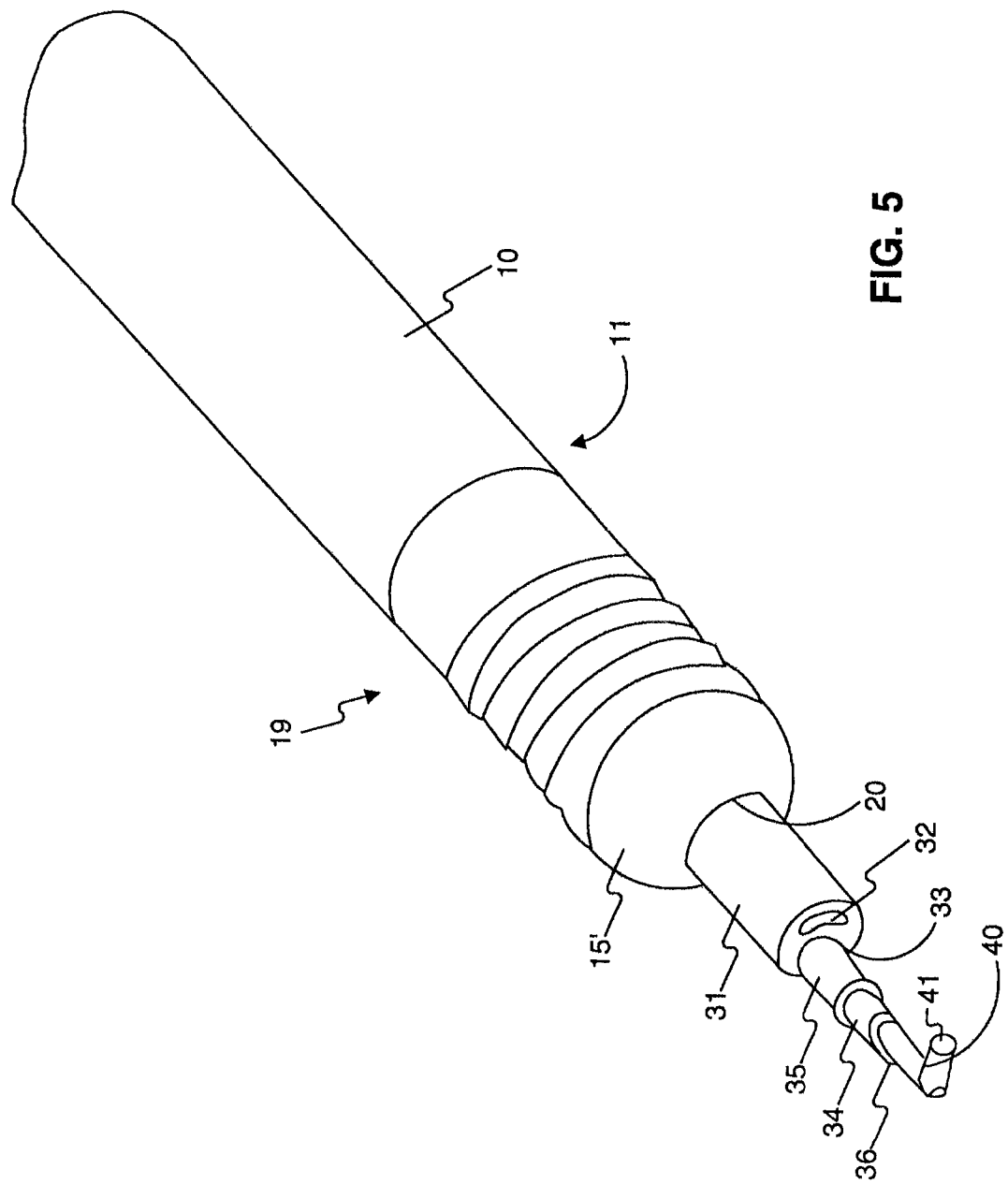
FIG. 5 is a perspective view of an endoscopic device according to a yet further embodiment of the invention.

FIG. 5 depicts an embodiment of a device 19 substantially similar to the device depicted in FIG. 4, with the added feature of a cutting tool 40. The cutting tool 40 may be configured to cut tissue, for example, by having a sharp edge 41. The cutting tool 40 (or knife) may be electrically active (i.e., monopolar or bipolar) so as to cut tissue and/or assist in cutting tissue, and may traverse the lumen 37 of the needle 34. When extended past the sharpened portion 36 of the needle 34, at least a portion of the cutting tool 40 may bend or be bent so that at least a portion of the cutting tool 40 is no longer substantially coaxial with the lumen 37 and/or needle 34. The cutting tool 40 may be made of a shape memory alloy or other similar material that causes the cutting tool 40 to bend once it is no longer axially constrained. The device 19, end effector assembly 11, electrode assembly 13, safety tip 15', and/or outer housing 31 may include an additional parallel passage to house a tool configured to allow the user to control the bending of the cutting tool 40. Instead of using lumen 37 of needle 34, the additional parallel passage may be used to advance the cutting tool 40 into the gastrointestinal tract, independent of the endoscopic tool 30, so as to permit crossing the cutting tool 40 with at least portions of the endoscopic tool 30, for example, the injection needle 34, and to permit simultaneous use of cutting tool 40 and injection needle 34.

Figure 22A:
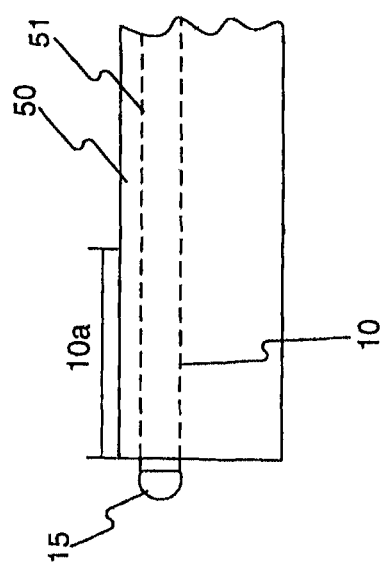
FIGS. 22A-22B are schematic views of another embodiment of the invention.
Figure 22B:
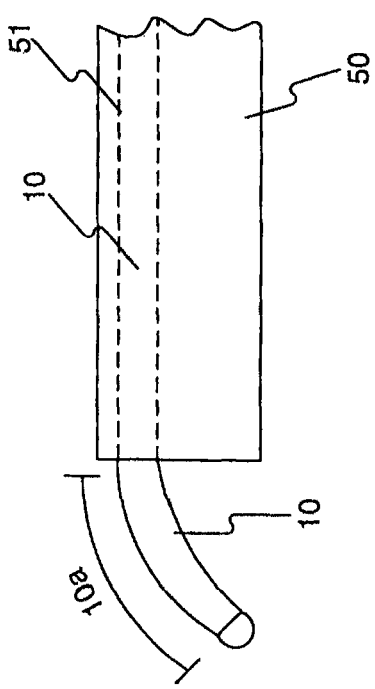

As shown in FIGS. 22A and 22B, a portion 10*a* of catheter 10 may be configured to curve when the portion 10*a* of catheter 10 is extended out of a lumen 51 of endoscope 50 within which catheter 10 may be disposed. Portion 10*a* may be made of a material configured to receive and retain a curvature, and may be made of substantially the same or different material as other portions of catheter 10. Such curving of the catheter 10 may assist various portions of the device 1 (e.g., the elongate member 17 and/or safety tip 15) in cutting and/or coagulating tissue.

As shown in FIGS. 11A and 11B, a sheath 52 may be coaxial with, and/or disposed over, and movable relative to at least a portion of catheter 10. Sheath 52 may be configured in that in a first configuration as shown in FIG. 11A, when sheath 52 is not disposed over at least a distal portion of catheter 10, catheter 10 may have a substantially straight configuration. However, when sheath 52 is in a second configuration as shown in FIG. 11B and disposed over at least a distal portion of catheter 10, catheter 10 may have a curved configuration. The portion 10A of catheter 10 that is curved when sheath 52 is deployed over it may be made of the same material or a different material (e.g., a softer material) than the rest of catheter 10. In various embodiments, however, the reverse also may be true. Thus, catheter 10, when unsheathed, may be made of a material that retains a preformed curve, however, when sheath 52 is advanced over catheter 10, catheter 10 may assume a substantially straight configuration.

Figure 18:
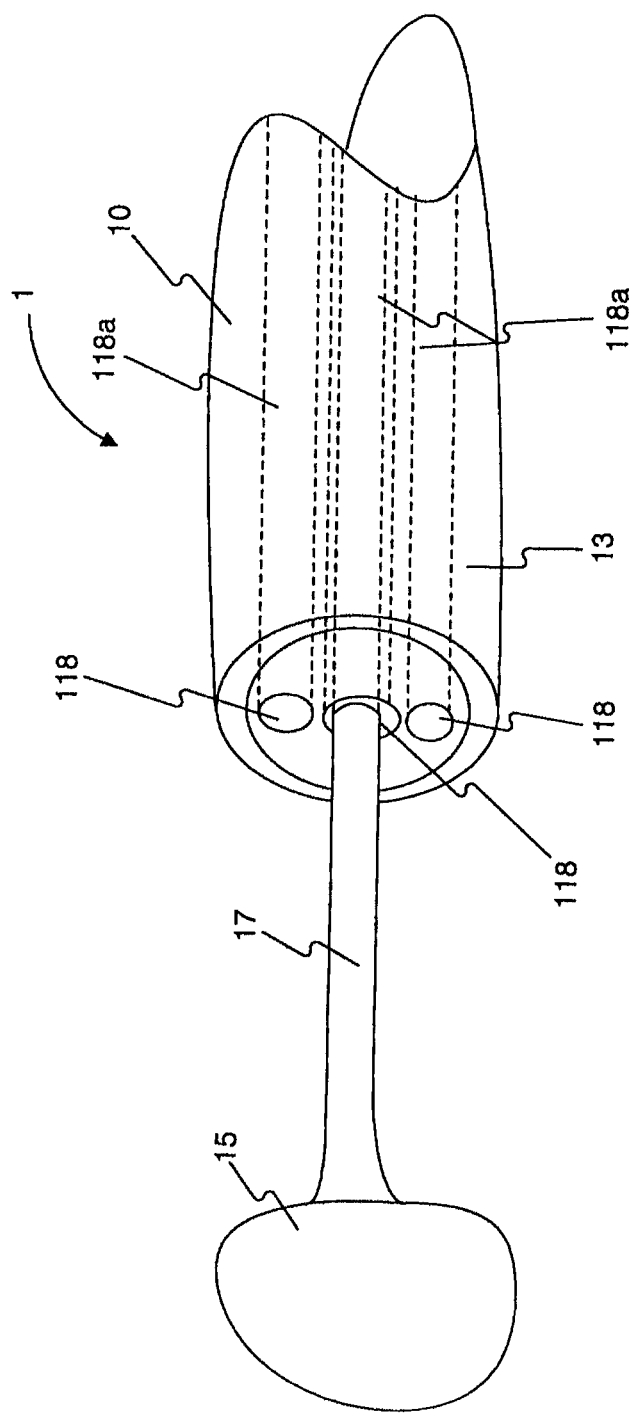
FIG. 18 is a schematic view of an endoscopic device according to a further embodiment of the invention.

Device 1, and more specifically end effector assembly 11 and its various components, as well as the catheter leading to the assembly 11, may have a variety of configurations. For example, as shown in FIG. 18, device 1 may include a non-electrically conductive safety tip 15 having a substantially spherical configuration, an elongate member 17 connected to an electrical power source and configured to cut tissue, and a monopolar electrode assembly 13 on the distal end of catheter 10. Monopolar electrode assembly 13 may have an outer diameter of about 2.6 mm, safety tip 15 may have a diameter of about 2.0 mm, and elongate member 17 may have a diameter of about 0.01 inches. Catheter 10 may include one or more ports 118 in flow communication with a respective channel 118*a*. One port 118 and channel 118*a* may be configured to accommodate elongate member 17 and allow elongate member 17 to move longitudinally relative to catheter 10. Another port 118 and channel 118*a* may be configured to irrigate fluid and/or aspirate debris therethrough. Another port 118 and channel 118*a* may be configured to accommodate a wire therethrough, for example, to connect monopolar electrode assembly 13 to a source of energy.

Figure 19:
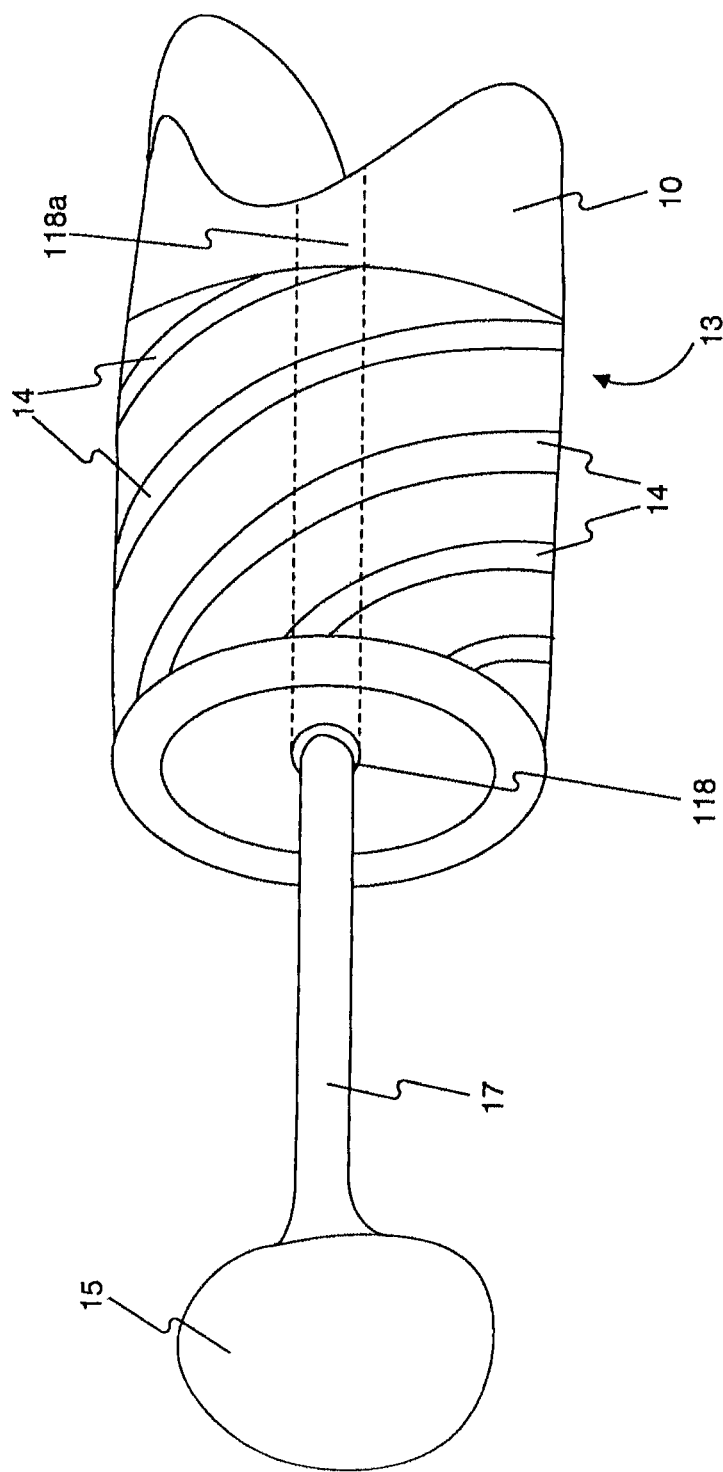
FIG. 19 is a schematic view of an endoscopic device according to yet another embodiment of the invention.

In another example, as shown in FIG. 19, device 1 may include an non-electrically conductive safety tip 15 having a substantially spherical configuration, an elongate member 17 connected to an electrical power source and configured to cut tissue, and a bipolar electrode assembly 13 with one or more spiral electrodes 14 disposed on the distal end of catheter 10. Bipolar electrode assembly 13 may have an outer diameter of about 2.3 mm, safety tip 15 may have a diameter of about 1.6 mm, and elongate member 17 may have a diameter of about 0.02 inches. Elongate member 17 may be disposed in a channel 118*a* of catheter 10, and may exit a distal end of catheter 10 through port 118 which is flow communication with channel 118*a*. Port 118 and channel 118*a* may be configured to allow elongate member 17 to move longitudinally relative to catheter 10.

In a further example, as shown in FIGS. 20A and 20B, device 1 may include a cautery tip 15 connected to a source of electricity and an elongate member 17 connected to an electrical power source and configured to cut tissue. FIG. 20A depicts a device 1 with no electrode assembly or cautery portion on the distal end of catheter 10. FIG. 20B depicts a device 1 with an electrode assembly 13 (e.g., cautery portion) on the distal end of catheter 10. Cautery tip 15 may be insulated from elongate member 17 by insulation 115. Safety tip 15 (e.g., cautery tip) may have a diameter of about 2.0 mm and elongate member 17 may have a diameter of about 0.025 inches. Catheter 10 may include one or more ports 118 in flow communication with their respective channel 118*a*. One port 118 and channel 118*a* may be configured to accommodate elongate member 17 and allow elongate member 17 to move longitudinally relative to catheter 10. Another port 118 and channel 118*a* may be configured to irrigate fluid and/or aspirate debris therethrough. Another port 118 and channel 118*a* may be configured to accommodate a wire therethrough, for example, to connect monopolar electrode assembly 13 to a source of energy. Elongate member 17 may include a lumen within which a wire 117 is disposed therethrough. Wire 117 may be electrically connected to both cautery tip 15 and a source of energy.

In various embodiments, device 1 may be configured to be advanced through a working channel of an endoscope. For example, the working channel may have a diameter of about 2.8 mm.

Figure 23A:
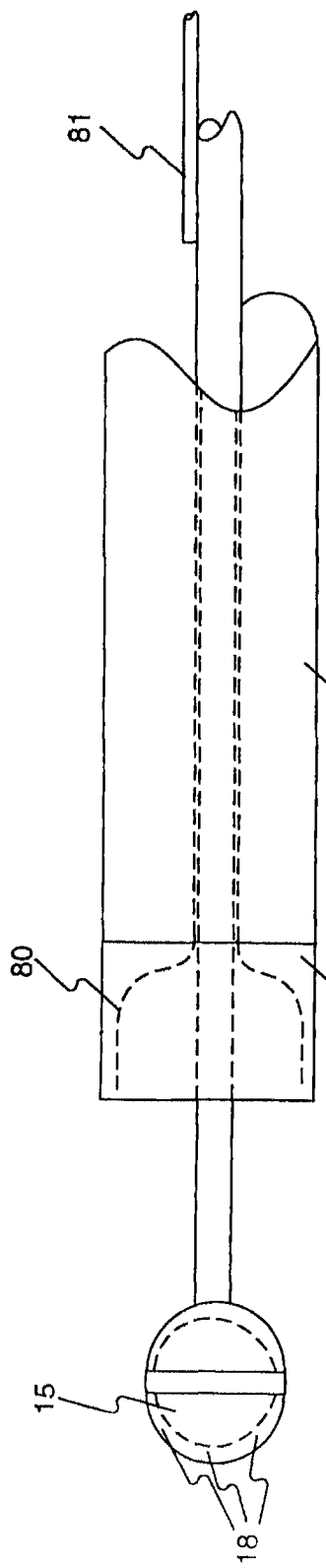
FIGS. 23A-23B are schematic views of a further embodiment of the invention.
Figure 23B:
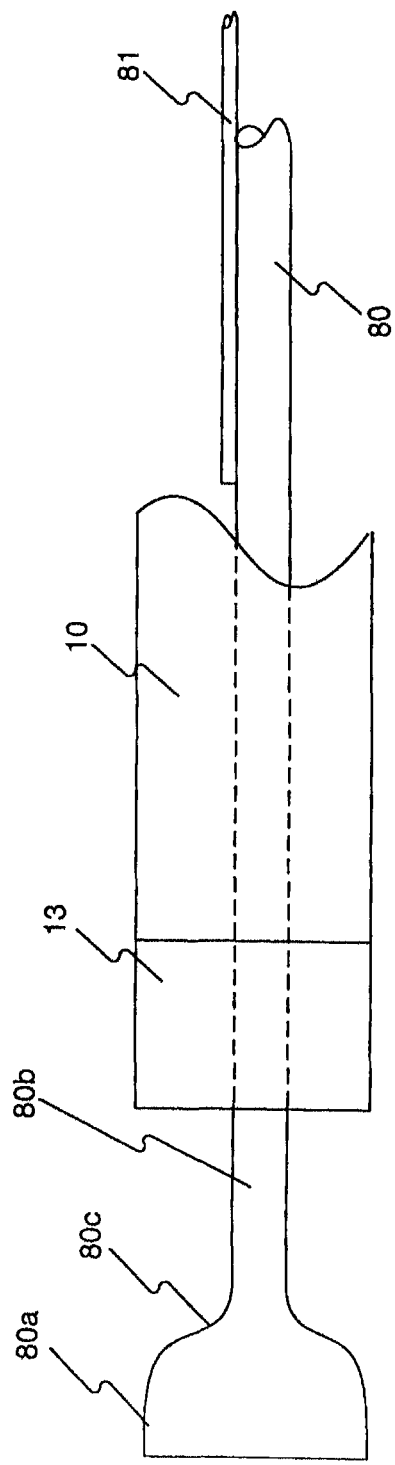
Figure 23C:
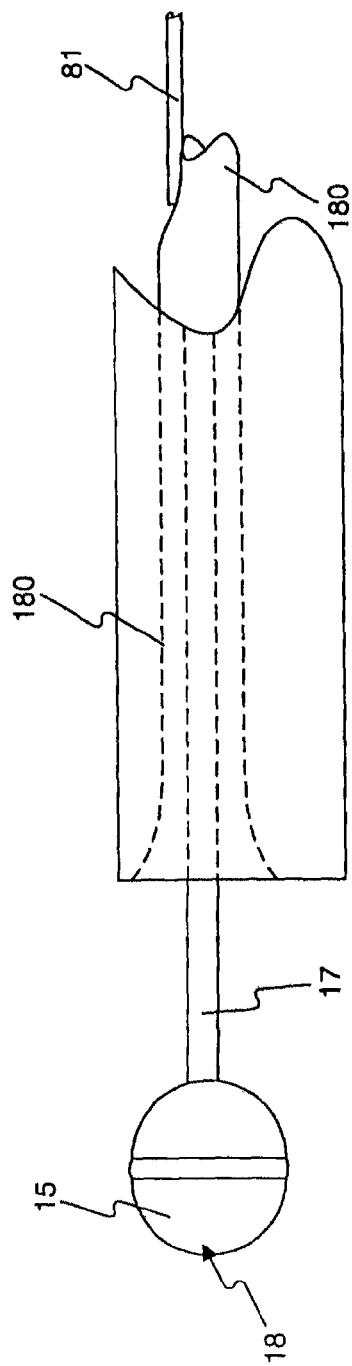
FIGS. 23C-23D are schematic views of yet another embodiment of the invention.
Figure 23D:
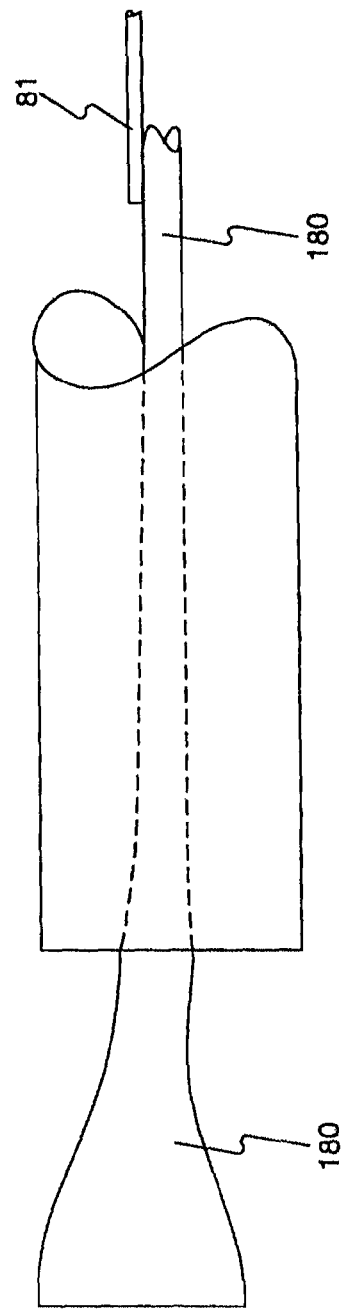

FIGS. 23A and 23B depict a device 1 including a cautery tip 15, an elongate member 17, a catheter 10, and a monopolar electrode assembly 13 disposed on a distal end of catheter 10. Cautery tip 15 may be hollow (e.g., to assist in dissipating heat) and may include one or more ports 18. Ports 18 may be configured to expel a fluid and/or gaseous medium out of hollow cautery tip 15*h*, and/or may be configured to remove a fluid and/or gaseous medium from the outside of device 1. Cautery tip 15 may be monopolar or bipolar. Elongate member 17 may be configured to cut tissue and/or may be connected to a source of energy. Device 1 may include a sheath 80. Sheath 80 may be made of any suitable non-conductive material and may be configured to move longitudinally relative to cautery tip 15 and/or elongate member 17. In a first configuration, as shown in FIG. 23B, sheath 80 may be configured to substantially cover cautery tip 15 and elongate member 17. For example, sheath 80 may be configured to cover all of cautery tip 15 and elongate member 17 except a distalmost portion of cautery tip 15. For example, sheath 80 may have a tip portion 80a configured to cover a proximal and surrounding portion of cautery tip 15, for example, by having a diameter larger than cautery tip 15. Sheath 80 may also have an elongate portion 80b configured cover at least a portion of elongate member 17. Sheath 80 may further have a transition portion 80c configured to cover a proximal portion of cautery tip 15 and a distal portion of elongate member 17. Transition portion 80c may conform to a shape of the proximal portion of cautery tip 15, for example, by having a substantially hemispherical shape. In a second configuration, as shown in FIG. 23A, sheath 80 may be configured to be substantially retracted into catheter 10, for example, such that a distal end of sheath 80 does not extend past a distal end of catheter 10. In such a configuration, cautery tip 15 and/or elongate member 17 may be substantially exposed. In another example, as shown in FIGS. 23C and 23D, sheath 180 may be made of any suitable expandable material. Accordingly, in a first configuration, sheath 180 may cover a proximal and surrounding portion of cautery tip 15, for example, by stretching until sheath 180 has substantially the same as or slightly larger than a diameter of cautery tip 15. Moreover, in a second configuration, sheath 180 may be substantially retracted into the catheter 10, and may have a diameter, at least along its distal portion, that is smaller than the largest diameter of cautery tip 15, but larger than the diameter of elongate member 17. Sheath 80, 180 may be connected to an actuator 81 (e.g., a pull wire) configured to move sheath 80, 180 longitudinally between the first configuration and second configuration. For example, if actuator 81 is in the advanced position as shown in FIGS. 23B and 23D, then sheath 80, 180 is covering cautery tip 15 and elongate member 17. In another example, if actuator 81 is in the retracted position, as shown in FIGS. 23A and 23C, then cautery tip 15 and elongate member 17 are exposed. A distal portion of catheter 10 may include a lumen configured to accommodate sheath 80.

In a method of using the endoscopic device 1, 19, the endoscopic device 1, 19 is advanced into a gastrointestinal tract, for example, the esophagus. The endoscopic device 1, 19 may be advanced into the gastrointestinal tract via a working port of an endoscope, or any other method known in the art. Once the endoscopic device 1, 19 and/or the end effector assembly 11 is placed at the desired portion of the gastrointestinal tract, the end effector assembly 11 or portions of the end effector assembly 11 may be actuated via a handle 9.

The electrode assembly 13 may be placed against a tissue section of the gastrointestinal tract, and then electrically activated so as to electro-coagulate the desired tissue section. Similarly, the safety tip 15, 15' (if conductive) may be placed against a tissue section of the gastrointestinal tract, and then electrically activated so as to electro-coagulate the desired tissue section. Such electro-coagulation may be desirable, for example, to reduce or prevent bleeding from the desired tissue section.

The elongate member 17 of the device 1 may be extended and then moved relative to a portion of the gastrointestinal tract, for example, an adenoma, so as to cut the adenoma from the gastrointestinal tract. The elongate portion 17 may be electrically activated so as to aid in the cutting of tissue.

Materials (e.g., gas(es), fluid(s), solid(s), or any combination of any of these elements) may be introduced into and/or aspirated from the gastrointestinal tract via one or more of the port 18, port 20, port 32, and lumen 37, for example, to flush out a portion of the gastrointestinal tract, determine whether an adenoma is attached to multiple esophageal layers, and/or perform any other therapeutic or diagnostic operation involving injection. The materials may be introduced into and/or aspirated from the gastrointestinal tract via one or more of the port 18, port 20, port 32, and lumen 37 while one or more of the elongate member 17, outer housing 31, outer jacket 35, and injection needle 34 is in either the extended or retracted configuration.

An endoscopic tool 30 may be advanced into the gastrointestinal tract via port 20. An injection needle 34 may be advanced past an outer housing 31 and/or an outer jacket 35 and into the gastrointestinal tract and/or a wall of the gastrointestinal tract, for example, to deliver drugs or any other substance into the wall of the gastrointestinal tract. The injection needle 34 may also be used to cut tissue from the gastrointestinal tract, for example, by placing the injection needle 34 in contact with the tissue and moving the injection needle 34 relative to the tissue.

A cutting tool 40 may be advanced into the gastrointestinal tract via port 20, port 33 of outer housing 31, lumen 37 of injection needle 34, and/or a passage parallel to any of the aforementioned ports and/or lumens described herein. The cutting tool 40 may then be actuated to cut tissue from a portion of the gastrointestinal tract, for example, by placing the cutting tool 40 in contact with the tissue and moving the cutting tool 40 relative to the tissue. The cutting tool 40 may be electrically activated so as to aid in the cutting of the tissue.

One or more of the port 18, port 20, port 32, lumen 37, or any other lumen of the device 1 may be configured to trap and/or capture tissue. For example, tissue may be trapped in port 37 as the needle 34 is advanced into the tissue. In another example, after tissue has been excised from the walls of the gastrointestinal tract, a vacuum may be created in port 20 so as to capture the tissue so that it may be removed from the gastrointestinal tract for further analysis.

In various embodiments, any of the aforementioned methods may be performed while one or more of the safety tip 15, elongate member 17, endoscopic tool 30, outer housing 31, outer jacket 35, injection needle 34, and cutting tool 40 is in either the extended or retracted configuration.

In various embodiments, any of the aforementioned aspects of any of the embodiments may be combined with any other aspect of any of the other embodiments. For example, an endoscopic device may include the cutting wire 17 and the cutting tool 40. Furthermore, aspects of the embodiments may be removed from the endoscopic devices. For example, the outer jacket 35 may be removed from the embodiments set forth in FIGS. 4-5.

The geometric and spatial configurations of various aspects of the embodiments depicted herein are exemplary only and may be rearranged as desired. For example, aspects of the devices do not have to be coaxial with each other. In another example, the electrode assembly need not be adjacent to the safety tip. In a further example, aspects of the invention may have geometric cross-sections of any desired shape and size.

The devices and methods set forth above may be used in any medical or non-medical procedure. For example, while the devices and methods set forth above are disclosed as being used in treating the gastrointestinal tract, they may also be used to treat any other suitable body lumen or organ.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for performing therapy on body tissue comprising:
    a catheter including a lumen extending therethrough;
    an end effector assembly at a distal end of the catheter and configured to cauterize tissue, the end effector assembly including a helical electrode assembly;
    a port extending through the end effector assembly and in communication with the lumen of the catheter; and
    a safety tip distal to the end effector assembly and configured to reduce damage to body tissue, wherein the safety tip includes an electrode and the port extends through the safety tip.

2. The device of claim 1, wherein the port is configured to pass at least one medical device therethrough, wherein the at least one medical device includes at least one of the following: a cutting wire, an injection needle, a needle knife, or a snare.

3. The device of claim 1, wherein the electrode of the safety tip is separately activatable from the helical electrode assembly.

4. A device for performing therapy on body tissue comprising
    a catheter including a lumen extending therethrough;
    an end effector assembly at a distal end of the catheter and having at least one discrete spiral electrode configured to cauterize tissue;
    a port extending through the end effector assembly and in communication with the lumen of the catheter; and
    a safety tip distal to the end effector assembly and configured to reduce damage to body tissue, wherein the safety tip includes an electrodes that is separately activatable from the discrete spiral electrode and the port extends through the safety tip.

5. The device of claim 4, wherein the safety tip includes a partial spherical distal tip.

6. The device of claim 4, wherein the port is configured to pass at least one medical device therethrough.

7. The device of claim 6, wherein the at least one medical device includes at least one of the following: a cutting wire, an injection needle, a needle knife, or a snare.

* * * * *